(12) United States Patent
Takanashi et al.

(10) Patent No.: US 11,307,153 B2
(45) Date of Patent: Apr. 19, 2022

(54) METHOD AND DEVICE FOR ACQUIRING TOMOGRAPHIC IMAGE DATA BY OVERSAMPLING, AND CONTROL PROGRAM

(71) Applicants: RIKEN, Wako (JP); Nissan Chemical Corporation, Tokyo (JP)

(72) Inventors: Takaoki Takanashi, Wako (JP); Shigeho Noda, Wako (JP); Masaru Tamura, Wako (JP); Yoshie Otake, Wako (JP)

(73) Assignees: RIKEN, Saitama (JP); Nissan Chemical Corporation, Tokyo (JP)

(*) Notice: Subject to any disclaimer, the term of this patent is extended or adjusted under 35 U.S.C. 154(b) by 0 days.

(21) Appl. No.: 17/059,002

(22) PCT Filed: May 28, 2019

(86) PCT No.: PCT/JP2019/021164
§ 371 (c)(1),
(2) Date: Nov. 25, 2020

(87) PCT Pub. No.: WO2019/230740
PCT Pub. Date: Dec. 5, 2019

(65) Prior Publication Data
US 2021/0262947 A1     Aug. 26, 2021

(30) Foreign Application Priority Data
May 28, 2018 (JP) .............................. JP2018-101218

(51) Int. Cl.
*G06T 11/00* (2006.01)
*G01N 23/046* (2018.01)

(52) U.S. Cl.
CPC .......... *G01N 23/046* (2013.01); *G06T 11/006* (2013.01); *G01N 2223/345* (2013.01); *G01N 2223/401* (2013.01)

(58) Field of Classification Search
CPC .... G06T 11/006; G06T 11/003; G06T 11/005; G06T 11/008
See application file for complete search history.

(56) References Cited

U.S. PATENT DOCUMENTS

2006/0232608 A1  10/2006  Riaz
2008/0130974 A1* 6/2008  Xu ..................... G06T 11/006
                                                   382/131
(Continued)

FOREIGN PATENT DOCUMENTS

CN    104899827 A    9/2015
JP    S63125242 A    5/1988
(Continued)

OTHER PUBLICATIONS

Arcadu et al., "A Forward Regriding Method with Minimal Oversampling for Accurate and Efficient Iterative Tomographic Algorithms," IEEE Transaction on Image Processing, 2016, vol. 25 (3), pp. 1207-1218.
(Continued)

*Primary Examiner* — Dani Fox
(74) *Attorney, Agent, or Firm* — Seed IP Law Group LLP

(57) ABSTRACT

In order to increase reproducibility of a reconstructed tomographic image without increasing the computational load, detection is performed by oversampling in (N+n) directions during imaging for detection by N detection elements. A vector having N×(N+n) elements is obtained, and vector decimation step is performed in which a total of n×N elements corresponding to a sequence {k} 30 denoting a decimation order are removed. In a discrete Radon transform step, a corresponding discrete Radon inverse matrix
(Continued)

$W_{SQ}^{-1}$ 40 is operated, and in an image data generation step, de-vectoring is performed, thereby tomographic image data are acquired. When oversampling is used, a discrete Radon inverse matrix $W_{SQ}^{-1}$ is obtained. Therefore, a tomographic image is obtained by matrix computation without resorting to iterative approximation.

20 Claims, 16 Drawing Sheets

(56) References Cited

U.S. PATENT DOCUMENTS

| 2013/0177225 A1* | 7/2013 | Zamyatin | G06T 11/006 |
| | | | 382/131 |
| 2017/0269008 A1* | 9/2017 | Sjolin | G01T 1/17 |

FOREIGN PATENT DOCUMENTS

| JP | 2008526283 A | 7/2008 |
| JP | 2016049455 A | 4/2016 |
| WO | 2013/105583 A1 | 7/2013 |
| WO | 2014/021349 A1 | 2/2014 |
| WO | 2014/185078 A1 | 11/2014 |
| WO | 2017/082785 A1 | 5/2017 |

OTHER PUBLICATIONS

Kawamura et al., "Optical Computed Tomography for Polymer Gel Dosimetry," Japanese Journal of Medical Physics., 2017, vol. 37 (2), pp. 111-116.

Deans, "The Radon Transform and Some of Its Applications," Krieger Publications Publication, 1983, pp. 121.

Kak, et al., "Principles of Computerized Tomographic Imaging," IEEE Press, 1988, pp. 73.

Siddon, "Fast calculation of the exact radiological path for a three-dimensional CT array," Medical Physics, 1985, vol. 12 (2), pp. 252-255.

Sunnegardh, et al., "A New Anti-Aliased Projection Operator for Iterative CT Reconstruction," 9th International Meeting of Fully Three-Dimensional Image Reconstruction in Radiology and Nuclear Medicine, 2009, pp. 125-127.

* cited by examiner tolerance t= 1/1

1/3

1/5

1/7

1/9

1/11

1/13

1/15

1/17

1/19 tolerance t= 1/1

1/3

1/5

1/7

1/9

1/11

1/13

1/15

1/17

1/19

METHOD AND DEVICE FOR ACQUIRING TOMOGRAPHIC IMAGE DATA BY OVERSAMPLING, AND CONTROL PROGRAM

BACKGROUND

Technical Field

The present disclosure relates to a method for acquiring tomographic image data by oversampling, an acquisition device, and a control program. More specifically, the present disclosure relates to an acquisition method, an acquisition device, and a control program for tomographic image data employing an efficient algebraic method of discrete inverse Radon transform based on oversampling.

Description of the Related Art

Tomography, or a tomographic imaging method using waves or particles having transmission nature such as X-rays, gamma rays, light waves, or waves or particles exhibiting any sort of permeability or transmission ability such as a seismic wave or other has been put into practical use. Typical examples include an X-ray CT scanner used in medical and industrial applications, SPECT (Single Photon Emission Computed Tomography), and Optical Tomography. In recent years, an optical CT device using visible light has been developed, and an imaging method using a gel dosimeter as an object is studied after its irradiation by radiation in order to verify three-dimensional distribution of radiation dose before performing radiation therapy of cancer. Mathematical principle assuring the tomographic image of the object by these imaging methods is Radon transform. In this context, the processing for capturing the attenuation rate of each part inside the object as imaging information from outside is described by Radon transform, and the processing for reconstructing the tomographic information of the object from the captured information is described by an inverse Radon transform. That is, the operation for detecting the flow of the wave or particles attenuated by the object at each position by changing the irradiation direction or the detection direction corresponds to the Radon transform. In contrast, an operation for reconstructing an image by estimating the attenuation rate of each part inside the object from the intensity information of each direction and each position of the detection corresponds to the inverse Radon transform. The Radon- or inverse Radon transform for continuous coordinates and continuous directions for real images is carried out using sampling points on coordinates or orientations for handling a finite number of pixels. The inverse Radon transform (discrete inverse Radon transform) for image reconstruction under sampled coordinates and orientations is reduced into solving multiple simultaneous linear equations or matrix operations. These mathematical aspects are described in standard textbooks (e.g., Non-Patent Documents 1 and 2).

Iterative reconstruction (IR), which is accompanied by iterative approximation to reduce noise and artifacts, has also attracted attention. The iteration process is repeated, for example, 100 times or more to obtain the solution. Such a technique for obtaining a reconstructed image by deriving an approximate solution of multiple simultaneous linear equations by relying on an algebraic method is called an ART (Algebraic Reconstruction Technique). The ARTs include techniques that are referred to as, for example, a Maximum Likelihood-Expectation Maximization (ML-EM) method, an Additive-Simultaneous Iterative Reconstruction Techniques (ASIRT), and a Multiplicative-Simultaneous Iterative Reconstruction Techniques (MSIRT). In conventional ARTs, a calculation scale becomes huge and a large amount of computational resources are required. In addition, repeated iterations often do not approach the solution corresponding to the true image and are captured by the local solution. On the other hand, approximation calculation efficiency in computing has been improved without resorting algebraic methods while utilizing realistic calculation resources. Such examples include FBP (Filtered Back Projection) (for example, Patent Document 1). Since the scale of the FBP calculation is smaller than ARTs, it is currently most frequently used with X-ray CT scanners.

In the course of the progress of the tomographic imaging methods from the beginning to date, there has been a continuing demand for increasing the number of imaging pixels, and therefore the possibility of the FBP has been intensively studied. The FBP is, however, generally disadvantageous in the quality of reconstructed images in which various artifacts are readily developed compared to IR. Nowadays, the ARTs, which are intrinsically advantageous in the quality of a reconstructed image, have been attracted much attention again based on continuing development of computational powers (see, for example, Patent Document 2).

CITATION LIST

Patent Documents

Patent Document 1: WO2014/021349
Patent Document 2: WO2013/105583
Non-Patent Documents
Non-Patent Document 1: Aviash, C Kak and Molcolm, Slaney, "Principles of Computerized Tomographic Imaging," IEEE Press (1988)
Non-Patent Document 2: Stanley R. Deans, "The Radon Transform and Some of Its Applications," Krieger Publications (1983)
Non-Patent Document 3: Robert L Siddon, "Fast calculation of the exact radiological path for a three-dimensional CT array," Medical Physics, vol. 12, no.2, pages 252-255 (1985)
Non-Patent Document 4: Sunnegardh, J. and Danielsson, P. -E. "A New Anti-Aliased Projection Operator for Iterative CT Reconstruction," 9th International Meeting of Fully Three-Dimensional Image Reconstruction in Radiology and Nuclear Medicine, pages 125-127 (2009)

BRIEF SUMMARY

Technical Problem

There is continuing need for quality of reconstructed images in addition to the quest for increasing the number of pixels for improving the quality of images. Even when a conventional ART is adopted in a situation in which the number of imaging pixels is increased, the number of dimensions of the simultaneous linear equation to be solved, or variables to be determined, is increased, which requires a huge scale of calculation resources and takes a long time for processing. Therefore, in order to seek practicability in image data acquisition processing by way of the conventional ART, all we can do is to wait for the improvement of the calculation capability. In particular, it is not practical to obtain a large number of tomographic images, for example, to obtain a three-dimensional volume image while relying upon the conventional ARTs, which requires re-execution for each imaging for the iterative calculation accompanying iterative approximation.

The present disclosure addresses at least some of the problems mentioned above. The present disclosure provides a high degree of practicality for high quality tomographic imaging methodology by employing a new sampling technique that is supported by an algebraic exact solution of the discrete inverse Radon transform, which is responsible for image reconstruction.

Solution to Problem

The inventors realized that the problem with conventional ARTs is due to their discretization procedures, such as sampling. Conventional ARTs contain a large number of overlapping equations in a multidimensional system of linear equations, and the number of available equations is practically insufficient in comparison with the number of variables to be determined. As a result, an iterative approximation has been required and the effort has been directed to the improvement of computation performance of processors. To address the above problem, the inventor has completed a new solution by re-examining it from the discretization method in which the unconventional sampling is combined with appropriate processing.

That is, in certain aspects of the present disclosure provided is a method for acquiring tomographic image data comprising: a step for disposing an object in a detection range of a detection device having N detection elements arranged in at least one row where N is a positive integer; a step of detection in which detection operations for obtaining an intensity value for each of the detection elements by receiving transmitted waves or particles by each of the detection elements are repeated, where the waves or particles are detectable by the detection device, over (N+n) directions (n is an integer greater than or equal to 1) that are not overlapped with each other in relative detection directions for the waves or particles viewed from the object, while irradiation of the waves or particles toward the detection device by an emission device is performed, or while the waves or particles not generated by the emission device are transmitted through each part of the object; a vectorization step for obtaining a first vector with N×(N+n) elements from a detection signal by the detection device in the detection operations, wherein the elements of the first vector corresponding to those obtained by vectorizing an oversampled sinogram with (N+n) rows and N columns, each row and each column of which are associated with each detection direction and each detection element, respectively; a vector decimation step of removing n×N elements corresponding a decimation order from the first vector to obtain a second vector having the remaining N×N elements; a discrete inverse Radon transform step of operating a discrete inverse Radon transform matrix to the second vector to obtain a third vector having N×N elements; and an image data generation step for obtaining image data, by de-vectorizing the third vector, for a two-dimensional tomographic image with N pixels×N pixels having a pixel arrangement that is stationary with respect to the object.

The present disclosure can also be implemented in an aspect of a tomographic image data acquisition device. Similarly, the present disclosure can be implemented in an aspect of a control program for a tomographic image data acquisition device.

Oversampling or oversample is based on the sampling concept of the digital signal processing theory, and refers to a process of sampling at a density higher than that of basic sampling. In particular, oversampling in each aspect of the present disclosure includes sampling the necessary angular range by selecting N+n sample points in the detection direction without overlap with each other, where N is the number denoting operative detection elements in a detection direction and n is an integer greater than or equal to 1. It should be noted that the number of detection elements denotes the number of operative elements, unless otherwise noted. Decimation refers to a process in which at least one of the elements of an oversampled matrix or the elements of a corresponding vector is discarded (removed) in subsequent computational processes. In the present application, including these, we may use terminology that follows the conventions of the art to which the disclosure belongs unless it renders the description unclear. Waves may include any sort of wave that can be conceived of as attenuated through propagation, such as electromagnetic waves, sound waves, and may include light waves (infrared, visible, and ultraviolet) and oscillations (e.g., seismic waves). Particles include any sort of particles that can be conceived of as attenuated through propagation in a stream of particle rays, including neutron rays and other radiation. Anything that may have properties both of wave and particle in a quantum mechanical sense, such as electrons and photons, is also included in either or both of the waves or particles. Similarly, anything that is regarded as waves or particles in a classical mechanics point of view is also included in one or both of the waves or particles. These waves or particles can be used in the practice of the present disclosure, even they are generated by a device or an emitting device, that is an artificial source of their emission, or may be generated from natural sources, for example, cosmic rays, or generated due to a property of the object, for example, radiation emitted from various parts of the interior of the object, which are referred to as "waves or particles that are not generated by the emitting device" in this application.

Advantageous Effects of Disclosure

In certain aspects of the present disclosure, a high-definition and high-quality reconstructed image can be acquired using a relatively small computational resources at a high speed.

BRIEF DESCRIPTION OF THE SEVERAL VIEWS OF THE DRAWINGS

FIGS. 2A to 2C illustrate a conventional technique and FIG. 2D depicts a device of the present embodiment.

FIG. 6A is a case where a random selection scheme is adopted, and FIG. 6B is a case where Gram-Schmidt orthogonalization is adopted.

FIG. 7A depicts an oversample system matrix $W_{OS}$ by an image, and FIG. 7B depicts a square system matrix $W_{SQ}$ obtained by decimation processing by block.

FIG. 8A indicates a discrete inverse Radon transform matrix $W_{SQ}^{-1}$, and FIG. 8B indicates a matrix obtained by operating the discrete inverse Radon transform matrix $W_{SQ}^{-1}$, on the square system matrix $W_{SQ}$ from the left.

FIG. 11D is a reconstructed image by a simple inverse Radon transform as a reference for comparison.

FIG. 12A is a photograph of the mouse sample, FIG. 12B is a reconstructed image using the pseudo-inverse matrix $W_p^{-1}$, FIG. 12C is a reconstructed image by FBP, FIG. 12D is a reconstructed image by ML-EM, and FIG. 12E is a reconstructed image by a simple inverse Radon transform.

FIGS. 13A-13J are ones with tolerance values indicated on each figure.

FIG. 14A is a photograph of the concrete sample, FIG. 14B is a reconstructed image using the pseudo-inverse matrix $W_p^{-1}$, FIG. 14C is a reconstructed image by FBP, FIG. 14D is a reconstructed image by ML-EM, and FIG. 14E is a reconstructed image by a simple inverse Radon transform.

FIGS. 15A-15J are ones with tolerance values indicated on each figure.

FIG. 16A indicates a pseudo-inverse matrix $W_p^{-1}$ obtained for the square system matrix $W_{SQ}$ in FIG. 7B, and FIG. 16B indicates a matrix obtained by operating the pseudo-inverse matrix $W_p^{-1}$ on the square system matrix $W_{SQ}$ from the left.

DETAILED DESCRIPTION

Figure 1:
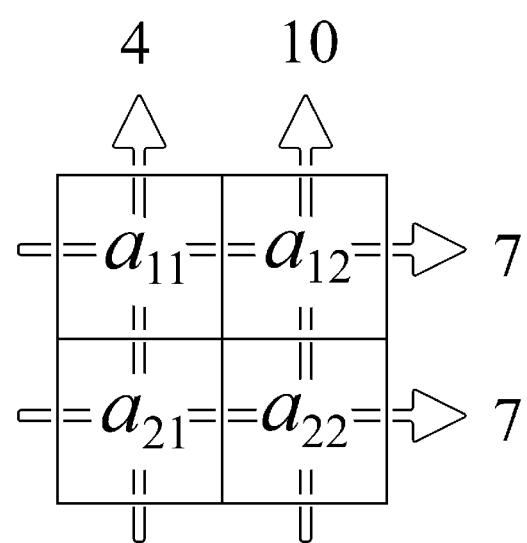
FIG. 1 is an explanatory diagram illustrating the principle of an algebraic method of a conventional discrete inverse Radon transform.

The embodiments of tomographic imaging according to the present disclosure will be described herein with reference to the accompanying drawings. For all drawings, the common reference numerals are given to common part or element unless otherwise noted. In addition, each element in the drawing should be understood as not being drawn to scale.

1. Principle

FIG. 1 is an illustration of the principle of the conventional algebraic method of discrete inverse Radon transform. The schematic illustrates the primitive nature of the process of irradiating a wave or particle and reconstructing a tomographic image using the intensity data after transmission. Each of the square areas arranged in 2 columns ×2 rows as illustrated should be associated with the pixels of the tomographic image, and these squares may have four values of $a_{11}$- $a_{22}$. These values carry the degree of beam attenuation by the object at the position of each pixel and are the values to be determined. White drawing arrows drawn through the plurality of pixels correspond to the irradiation of the wave or particle beams and the positions of the detection elements. Each numerical value pointed by each arrow mean a value (e.g., degree of attenuation) obtained when the detection element of the detection device is positioned ahead of the arrow, and the sum of the values of the pixels passed here is indicated by the numerical value. That is, the arrows represent the beams of the wave or the particle, and the pixels passed by the arrows and the directions of the arrows indicate the irradiation and detection (hereinafter it may be referred to as "irradiation"). The total value pointed by the arrow corresponds to the attenuation component detected by each detection element, which is positioned ahead of the arrow. Determining the four values of $a_{11}$- $a_{22}$ only by values pointed by the allows, or values obtained from the detection device, corresponds to executing a discrete inverse Radon transform on the basis of the values indicated by the detection elements of the detection device for reconstructing the tomographic image.

In the example shown in FIG. 1, one of $a_{11}$- $a_{22}$ connected by an arrow gives a linear sum, so that it can be written in a simultaneous equation. When the simultaneous equations are solved, the solution is the following:

$$a_{11} = 4 - a_{21}$$

$$a_{12} = 3 + a_{21}$$

$$a_{21} = \text{any value}$$

$$a_{22} = 7 - a_{21}$$

That is, the number of equations (variables to be determined) is 4, whereas the substantial number of simultaneous equations that can be derived by the irradiation as indicated by the arrow is 3. Since the above simultaneous equations are satisfied even when $a_{21}$ is substituted by any value, the four values of $a_{11}$ to $a_{22}$ become indeterminate, which means these values cannot be determined.

Figure 2A:
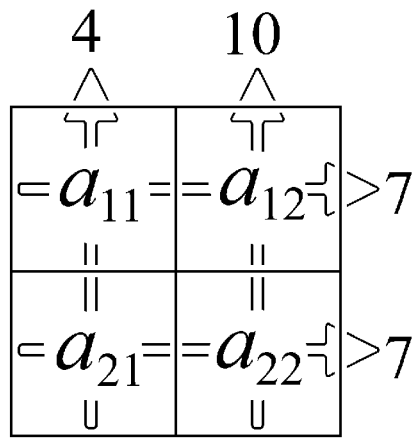
FIGS. 2A to 2D indicate explanatory diagrams illustrating principles of an algebraic method of a discrete inverse Radon transform according to embodiments of conventional and the present disclosure.
Figure 2B:
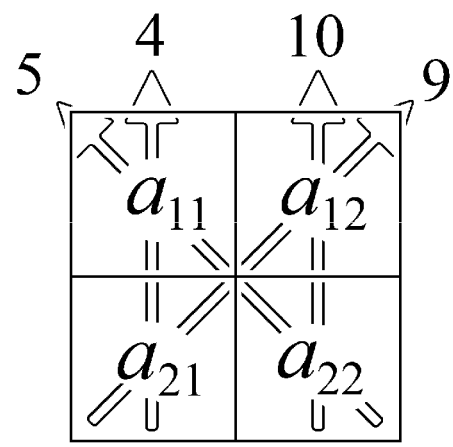
Figure 2C:
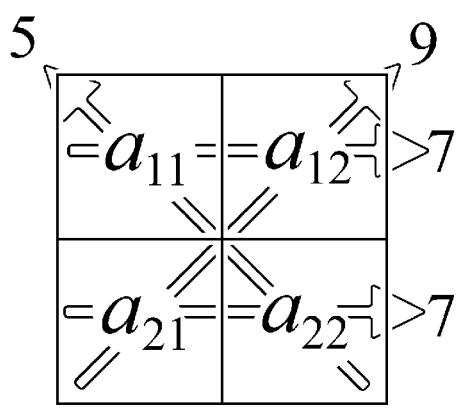

FIGS. 2A to 2D indicate explanatory diagrams illustrating principles of an algebraic method of a discrete inverse Radon transform according to embodiments of conventional and the present disclosure. FIG. 2A is equivalent to FIG. 1, FIGS. 2B and 2C illustrate another conventional approach, and FIG. 2D reflects the design of the present embodiment. The solutions of FIGS. 2A to 2D are summarized in Table 1.

TABLE 1

Figure 2D:
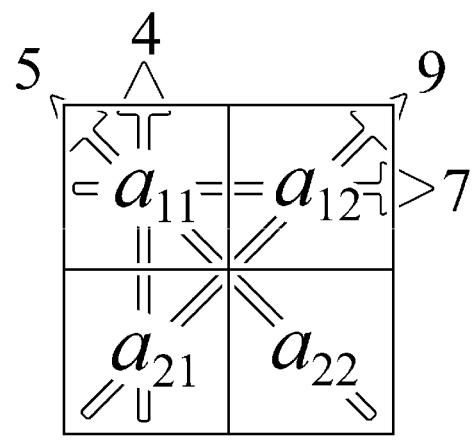

|  | $a_{11}$ | $a_{12}$ | $a_{21}$ | $a_{22}$ |
| --- | --- | --- | --- | --- |
| FIG. 2A (FIG. 1) | $4 - a_{21}$ | $3 + a_{21}$ | any value | $7 - a_{21}$ |
| FIG. 2B | $4 - a_{21}$ | $9 - a_{21}$ | any value | $1 + a_{21}$ |
| FIG. 2C | $4 - a_{21}$ | $9 - a_{21}$ | any value | $7 - a_{21}$ |
| FIG. 2D | 1 | 6 | 3 | 4 |

As shown in Table 1, four values of $a_{11}$-$a_{22}$ in FIGS. 2B and 2C cannot be determined, as in the case of FIG. 2A (FIG. 1). That is, even if a simultaneous equation is created by altering the combination of variables by using irradiation in the diagonal direction, it is not always be possible to determine the four values of $a_{11}$ to $a_{22}$ in FIGS. 2B and C. On the other hand, when irradiation is performed as shown by an arrow in FIG. 2D, the four values of $a_{11}$ to $a_{22}$ can be uniquely determined. It is to be noted that the group of arrows in FIG. 2D is mere combined and selected ones from arrows in FIGS. 2A-2C, that is irradiation azimuths and detection elements. In FIG. 2D, the number of arrows indicating the number of simultaneous equations to be solved is not increased. In spite of this, four values are specified in the case of FIG. 2D. We believe that such a difference is caused by symmetry. In other words, since the symmetry of the detection directions or the detection elements is high in the cases of FIGS. 2A to 2C, whereas the symmetry breaking occurs in the case of FIG. 2D, therefore the values can be specified in an algebraic method there. This difference suggests that appropriate design in the step of irradiation would allow us to obtain a solution through an algebraic method even in a multiple simultaneous linear equation having a more general form for reconstruction processing of a real tomographic image. The inventors of the present application noted that oversampling is performed in the step of irradiation (discrete Radon transform) and thereafter decimation is carried out, it is possible to intentionally realize breaking of symmetry, which provides us with a non-indefinite, strict solution by an algebraic method.

Figure 3:
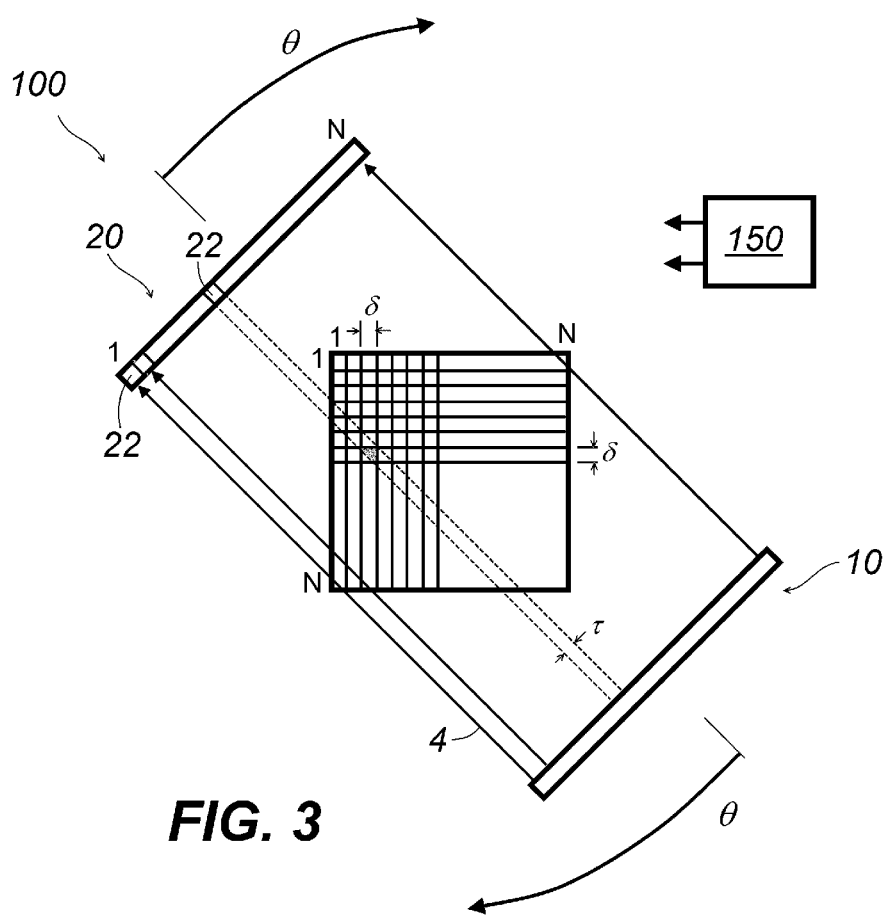
FIG. 3 is a schematic diagram for explaining a schematic configuration in an embodiment of the present disclosure, where the schematic configuration includes a plane arrangement on a cut surface of an object to be imaged in an example tomographic imaging device.

The exemplary geometrical arrangement of the present embodiment will now be described. FIG. 3 is a schematic diagram for explaining a schematic configuration including a plane arrangement on a cut surface of an object to be imaged in an example tomographic imaging device 100 in which an image of the present embodiment is acquired. A group of pixels having N pixels×N pixels is defined on one plane of a space that is stationary with respect to an object (not shown in FIG. 3). Typically, the integer N is matched with the number of detection elements 22 of the detection device 20. Therefore, in this embodiment, the integer N is sometimes referred to as resolution N. The beam 4 of a wave or a particle is included in the plane, and is emitted from the emission device 10. The detection device 20 and the emission device 10 can rotate relative to the object while the relative arrangement is fixed. For operation and calculation processing of a device including such control, the tomographic imaging device 100 is provided with a control device 150 which can be a computer device. The rotation is relative to the group of pixels and the object stationary therein. Thus, the detection device 20 and the emission device 10 are not always rotated; instead, it is possible that the detection device 20 and the emission device 10 are fixed to the installation floor surface (not shown), and the object may be rotated together with the group of pixels.

The operation for irradiating with the beam 4 and detecting the beam 4 on the opposite side of the object by the detection device 20 in conventional methods use sampling in the detection direction by dividing the scanning range of the detection direction 0 by the number N of pixels. The scanning range of the detection direction $\mathbf{0}$ is, for example, 0° to 180° in parallel with the beam 4 as shown in FIG. 3; conventional methods use $(180/N)°$ interval in sampling the detection signal from the detection device 20. The typical scanning operation of the detection direction θ of the tomographic imaging device 100, including the present embodiment, is performed with sampling by electrically controlling timings of acquiring values of the detection device 20 while performing constant-speed rotation, or increasing or decreasing the angle of direction θ at a constant speed. However, the present embodiment is not limited to such an operation.

The beam 4 has a spread covering all the pixel ranges at the coordinates, and a part directed to each detection element 22 has a width τ. The contribution of the pixel for the beam 4 related to the detection element 22 is typically the overlap of the width τ and each pixel (with vertical and horizontal lengths of δ), where the width is of the part of the beam 4 directed toward one of the detection elements 22. This overlap is illustrated in FIG. 3 by a pixel with a pattern. For all of the N×N pixels, the contribution is determined for each detection element 22 for each detection direction θ. The system matrix W holds these contributions as numerical values. Among the irradiation and the image reconstruction, the discrete Radon transform representing the irradiation is performed using the system matrix W by the multiplication operation using a matrix, which is expressed as $$X' = WX \quad (1)$$

In this case, the system matrix W is usually arranged in the row direction for the sampling points in the space corresponding to the total number of pixels and in the column direction for the sampling points in the irradiation and in the detection corresponding to the interval in the detection direction and the detection elements. When a conventional technique is applied to setting such as the number of pixels in FIG. 3, the system matrix W becomes a square matrix having N×N elements both in the row and column directions, which makes the number of the elements to $N^4$. This is because there exist N×N pixels for the entire pixels, N samples for the scan range of the detection direction θ, and N elements for the number of detection elements 22. It should be noted that the value N has increased with times in order to improve the image quality, and in a typical example, the value of N is set to about 1024, or $\sim 10^3$. The maximum value N is about 2000 in a conventional technique. However, the value of N is not limited specifically in the present embodiment. In the case where N is about $10^3$, the system matrix has a scale of about $10^3$ both in the row and column directions, and the number of elements is about $10^{12}$.

In Formula (1), X represents an attenuation image, which is an image representing attenuation (including absorption and scattering) at the position of each pixel, as a column vector. Although the attenuation image in the actual space is the two-dimensional image of the N×N pixels shown in FIG. 3, X is a vector for calculation with the system matrix W, where the vector is obtained by vectorizing the row direction into the total number of pixels, N×N pixels. In Formula (1), a column vector X' on the left side obtained by operating the system matrix W to the attenuation image X corresponds to an image called sinogram. In response to the arrangement in the system matrix W, where the sampling points along the detection direction are associated to a column direction, the column vector X' also indicates the detection intensity obtained for each of the sampling points in the detection direction and each of the detection elements. The sinogram is obtained by rearranging the elements of the column vector X' into two-dimensional with the axis of the detection element and the axis in the detection direction. As described above, Formula (1) is formulating irradiation and detection. In the figures shown in FIGS. 2A-2D, the column vector X corresponds to each value of $a_{11}$ to $a_{22}$, and the column vector X' corresponds to a value pointed by each arrow, and the system matrix W reflects the correspondence between each arrow and each pixel.

The reconstruction of the tomographic image is a process for calculating a column vector X from a column vector X' for the sinogram and the system matrix W and obtaining an attenuation image from the column vector X, on the assumption that the expression (1) is realized. That is, the reconstruction of the tomographic image is expressed by the following formula:

$$X = W^{-1} X'. \quad (2)$$

Here, $W^{-1}$ is the inverse matrix of W, and the Formula (2) is obtained by operating $W^{-1}$ on both sides of the Formula (1) and replacing the right and left hand sides. In practice, it is not always that a square matrix W has an inverse matrix $W^{-1}$ (or, a regular matrix). The fact that the respective values of $a_{11}$-$a_{22}$ are not determined in FIGS. 2A-2C means that $W^{-1}$ does not exist for such irradiation and the detection manners, whereas the fact that the values of $a_{11}$-$a_{22}$ can be determined in FIG. 2D means that $W^{-1}$ does exist. That is, the availability of the idea that the break of symmetry in FIG. 2D is adopted is equivalent to the possibility that the system matrix W, which is a square matrix having an inverse matrix $W^{-1}$, can be determined with sufficient certainty. In the present embodiment, what is proposed is a method capable of surely determining a system matrix W having an inverse matrix $W^{-1}$, and also proposed is a realistic structure having sufficient practicality for irradiation, detection and tomographic image reconstruction for the method. Although the description based on FIG. 3 is for irradiating a parallel beam, the present embodiment can be applicable to an emission device 10 or a detection device 20 that use a non-parallel beam such as a fan beam or a cone beam, with a slight change in a way apparent to a person skilled in the art. In addition to setting such as the number of pixels in FIG. 3, the method of the present embodiment can be applied. The Formulas (1) and (2) can also be expressed in another mathematically equivalent format. For example, for the system matrix W, the arrangement of sampling points for the space corresponding to the total number of pixels is associated to the column, and the arrangement of the sampling points for the irradiation and detection corresponding to the interval in the detection direction and the detection element is associated to the row direction. As a result, X in the formula (1) can be expressed as a row vector according to the position of each pixel. In this case, the expressions corresponding to the Formulas (1) and (2) are subjected to transpose operation on each side. In this transpose operation, the rows and columns of the matrix and the vector are exchanged, and the matrix operation to the vector is apparently changed especially on its order, from "left to right" to "right to left". When the vector is described in an alternative statement as a "column or row vector" and the array of elements of the corresponding matrix is described in a similar alternative statement as in the "column direction or row direction", the alternative elements are taken up according to the order in such alternative descriptions. Since the selection of the statements does not affect the essence of the present application, X or the like obtained by vectorizing sinogram as in Formula (1) is expressed by a column vector, and the matrix of the system matrix or the like will be described on the basis of notation to operate as left-to-right manner, unless otherwise noted.

2. Specific Structure

In this embodiment, a system matrix W, which is a regular square matrix capable of having the inverse matrix $W^{-1}$, can be determined with certainty so that the Formula (2) will be held in the end. For distinction purposes in this embodiment, the system matrix W of the square matrix is referred to as a square system matrix and expressed as $W_{SQ}$.

2-1. Over Sampling and Decimation

Figure 4:
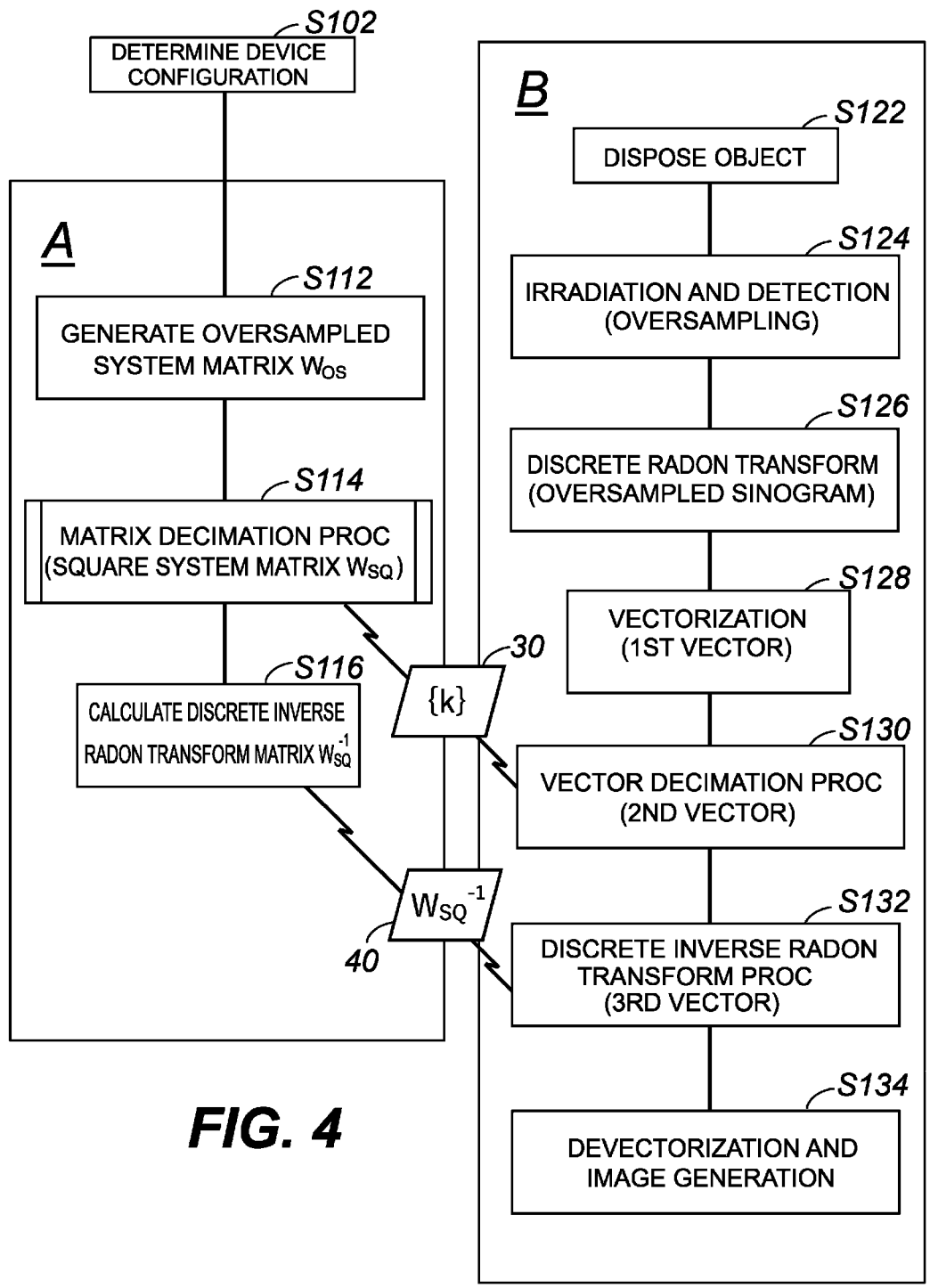
FIG. 4 is a flowchart indicating a process performed in a control device of a tomographic imaging device according to an embodiment of the present disclosure.
Figure 5:
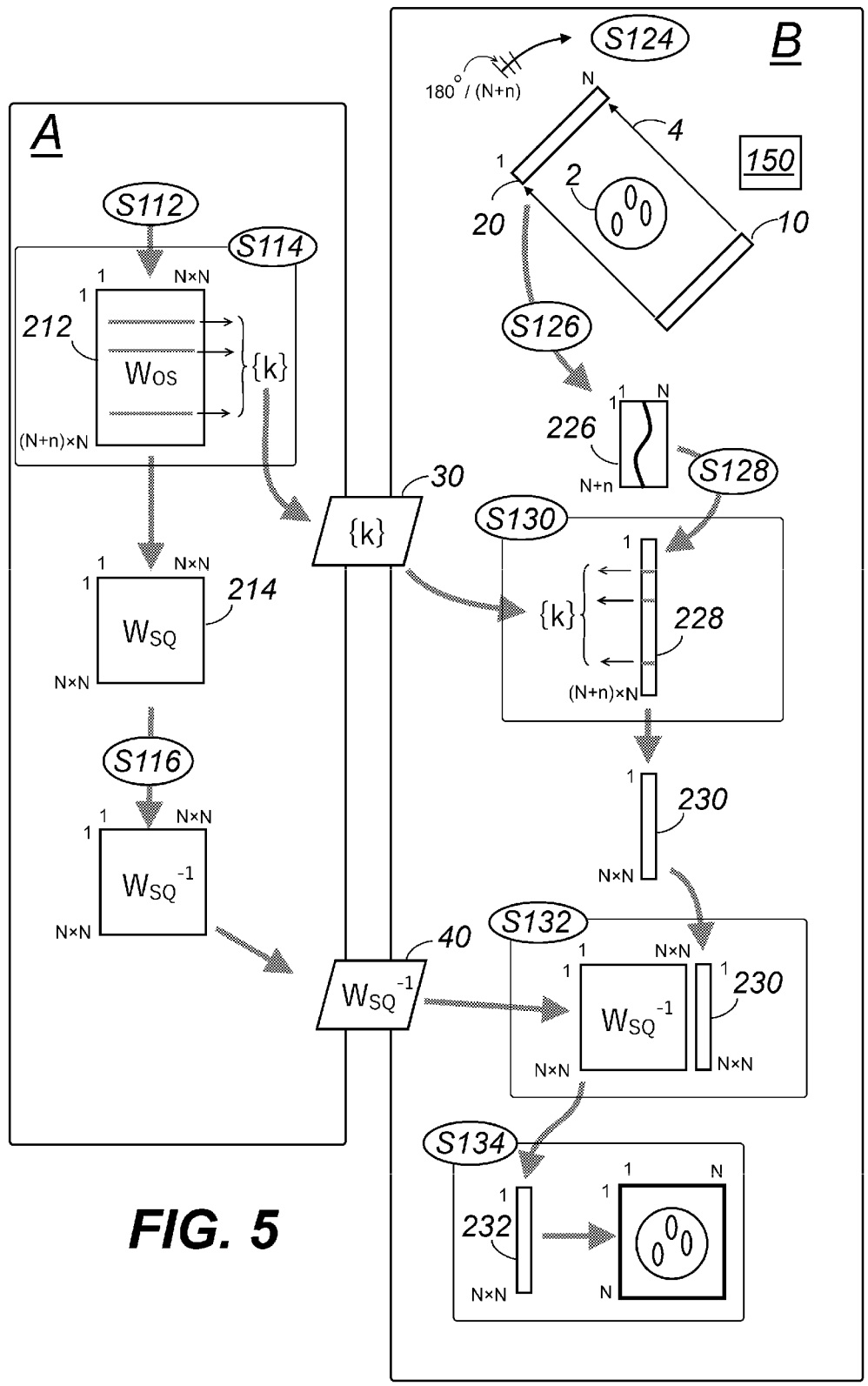
FIG. 5 is an explanatory diagram schematically indicating a series of transformations of a matrix, a vector, or an image obtained at each stage of a processing flow chart (FIG. 4) in a tomographic imaging device according to an embodiment of the present disclosure.
Figures 6A, 6B:
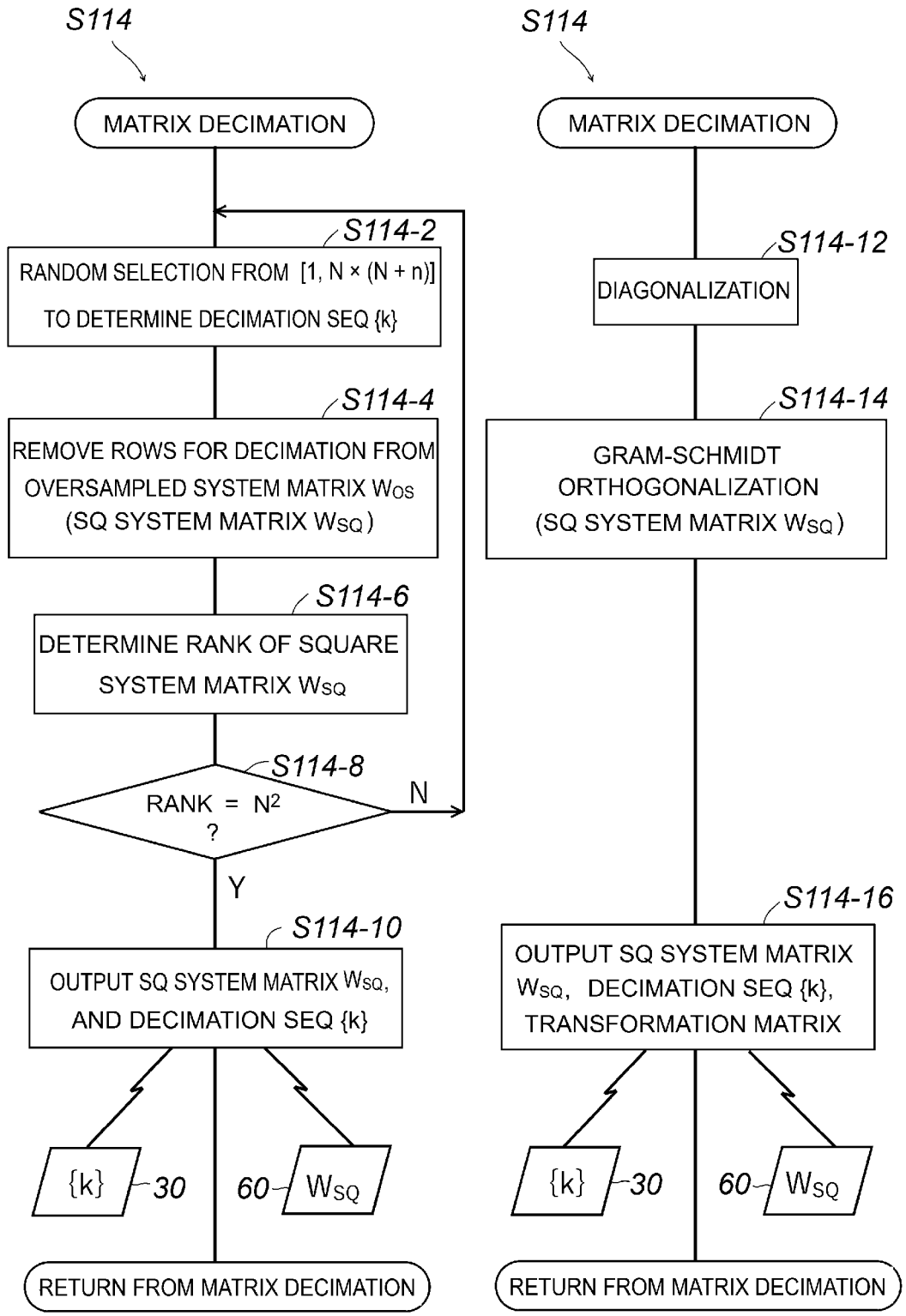
FIGS. 6A to 6B indicate flowcharts of matrix decimation processes according to various embodiments of the present disclosure.

A regular square system matrix $W_{SQ}$ is obtained as oversampling and decimation (thinning processing) are performed in this embodiment. FIG. 4 is a flowchart for overview of processing performed in a control device 150 of the tomographic imaging device 100 of the present embodiment including the oversampling and decimation, and FIG. 5 is an explanatory diagram schematically indicating a series of transformations of a matrix, a vector, or an image obtained at each stage of the processing of the flowchart. FIGS. 6A to 6B indicate flowcharts depicting matrix decimation processes; FIG. 6A is a case where a random selection scheme is adopted, and FIG. 6B is a case where Gram-Schmidt orthogonalization is adopted.

2-2. Overview of Processing

In an overview of the process performed in this embodiment, the configuration of the device is first determined (FIG. 4, S102). When a two-dimensional image of N pixels×N pixels (N is a positive integer) is reconstructed in the later imaging, the number of detection elements 22 of the detection device 20 is also determined to be N. The sampling for the detection direction θ is done in the conventional method in increments of, for example, (180/N)° , as described above, so that the sampling is carried out for N directions that does not overlap within the required range, such as 0 to 180° , for example. In contrast, the sampling of the detection direction θ in this embodiment is made for N +n directions (n is an integer greater than or equal to 1), which is non-overlapping within the required range, e.g., in increments of (180/(N+)n)°). This n is determined appropriately according to the number of elements of the detection element N, or the number of pixels on one side of the tomographic image, at the stage of determining S102 of the device configuration. The sampling adopting the detection direction in N+n directions in this regard, instead of N directions, is called oversampling. Here, n is also specifically referred to as an oversampling amount.

In order to obtain a proper reconstructed image from the object 2, the system matrix must be determined in accordance with the oversampling. The system matrix is generated by the same process as the conventional system matrix shown in FIG. 3 for N+n detection directions in the case of oversampling (S112). The system matrix obtained here has N×(N+n) elements in the column direction corresponding to the detection direction and each detection element, and N×N elements in the row direction corresponding to the number of pixels in the tomographic image. This non-square matrix is referred to as an oversampled system matrix in this embodiment and is denoted by $W_{OS}$. FIG. 5 schematically illustrates this oversampled system matrix $W_{OS}$ (ref 212). This oversampled system matrix $W_{OS}$ 212 is stored in the oversampled system matrix storage unit 50. In the next matrix decimation process S114, the elements of the N×n row vectors in the proper position (in decimation order) of the matrix are removed from the oversampled system matrix $W_{OS}$ 212 to produce the square system matrix $W_{SQ}$ (FIG. 5, ref. 214). This square system $W_{SQ}$ 214 is stored in the square system matrix storage unit 60. At that time, the number sequence {k} (hereinafter referred to as the "decimation sequence {k}") that gives the decimation order is also stored in the decimation sequence storage unit 30. If the decimation sequence {k} is appropriate one, the square system matrix $W_{SQ}$ becomes a regular matrix. From the square system matrix $W_{SQ}$, its inverse matrix $W_{SQ}^{-1}$ is calculated in the discrete inverse Radon transform matrix calculation step S116 and stored in the discrete inverse Radon transform matrix storage unit 40. In this embodiment, the inverse matrix $W_{SQ}^{-1}$ is also referred to as the discrete Radon inverse matrix. For the process of calculating the inverse matrix $W_{SQ}^{-1}$ here, any method such as the cofactor factor method or the sweep-out method, for example, can be employed.

On the other hand, to obtain a tomographic image from the object, the object 2 is placed between the emission device 10 and the detection device 20 having each detection element 22 (S122, FIG. 5). For conducting oversampling with the irradiation and detection operation, the detection is performed in non-overlapping N+n directions with n as an integer greater than or equal to 1 (S124) while the beam 4 from the emission device 10 is irradiated (S124). In a typical implementation, this beam 4 irradiates continuously, while the orientation of the object 2, the emission device 10, and the detection device 20 (direction of detection) moves smoothly while the signal from the detection element 22 of the detection device 20 is electrically sampled. A typical example of the irradiation and detection in the non-overlapping N+n directions is sampling in (180/(N+n))° intervals. The obtained signals are organized into data that can be used to generate a sinogram (S126), if necessary, by processing corrections and scale conversions for physical characteristics of the instruments and arranging the sequence order. Since the arranged data is oversampled with respect to the detection direction by corresponding to the detection direction and the position of the detector, it is called an oversampled sinogram in this embodiment (FIG. 5, ref. 226). The process of obtaining the oversampled sinogram 226 is the irradiation and detection process, which is the discrete Radon transform. From this oversampled sinogram 226, a column vector can be obtained by rearranging the elements in such an order as to match the column order of the oversampled system matrix $W_{OS}$ 212 (Vectorization S128). This vector is referred to as a first vector 228 in this embodiment (FIG. 5). The first vector 228 has N×(N+n) elements because it has the values of an oversampled sinogram. The first vector 228 can be said to be a column vector that would be obtained by operating the oversampled system matrix $W_{OS}$ 212 to a column vector of the tomographic image (the column vector of N×N elements) as in Formula (1), if a tomographic image were obtained and vectorized. The first vector is also referred to as $X_{OS}'$. From irradiation and detection S124 to vectorization S128, quantization by analog-to-digital conversion of the signal and processing of the digital signal and temporary storage of the data can also be done if necessary. Obtaining an oversampled sinogram is sufficient if necessarily data for generating it is obtained, thus it is not necessary to display it, nor is it necessary to go through explicit data that can be identified as an oversampled sinogram. If a first vector corresponding to the vectorized oversampled sinogram is obtained based on the detection signal from the detection device 20, any process that performs any equivalent processing from irradiation and detection S124 to vectorization S128 is also included in this embodiment.

A vector decimation process (S130) for decimating the elements of the first vector $X_{OS}'$, following an identical decimation order in which the square system matrix $W_{SQ}$ was obtained, will yield the second vector 230, which is a column vector with N×N elements that can satisfy the relationship of Formula (1) between the square system matrix $W_{SQ}$. The second vector is also denoted by X'. Since the second vector X' satisfies the relationship of Formula (1) with the square system matrix $W_{SQ}$, the relationship of Formula (2) holds using the discrete Radon inverse matrix $W_{SQ}^{-1}$, which is the inverse of the square system matrix $W_{SQ}$, and the discrete inverse Radon transform process S132 gives the third vector 232 for the reconstructed image. This third vector 232 is also denoted as X. The reconstructed image is obtained by de-vectorization of the sequence of the third vector X back to an N×N pixels image, which is an inverse operation of vectorization (S134). This conducts reconstruction of the tomographic image for one slice, so the process can be performed with the slice position changed if necessary.

The present embodiment is divided into two sections A and B of processes shown in FIGS. 4 and 5. A user who normally captures the reconstructed image performs section B of the processes leading from irradiation and detection step S124 to imaging step S134. Namely, the user does not necessarily have to perform section A of the processes leading from the determination of the device configuration S102, the system matrix generation step S112 to the discrete inverse Radon transform matrix calculation step S116. Section A of the processes leading from the system matrix generation step S112 to the discrete inverse Radon transform matrix calculation step S116 is required for a situation in which the tomographic imaging device is manufactured, installed and maintained, by the equipment manufacturer or the like. If the decimation sequence {k} and the discrete Radon inverse matrix $W_{SQ}^{-1}$ are obtained for a predetermined oversampling amount n, the user who intends to image the reconstructed image need only use them for their own measurements. If data on the appropriate instrumental information from section A are obtained, it can be used to adequately perform the processing of the scope of section B.

It should be noted that among the section B, the discrete Radon transform S126 to the imaging step S134 is the transposition of the order of matrices and vectors and the operation of the matrix multiplication and does not include within its scope the processing that is problematic in terms of computational processing volume, such as an iterative approximation, as an example. In this embodiment, the processes in section B, which are used in the user's ordinary imaging, can be performed with a sufficiently light computational burden merely using the decimation sequence storage unit 30 and the discrete inverse Radon transform matrix storage unit 40 prepared by the processing of section A. This brings a high degree of practicality to this embodiment. This is because the computational burden of the most intensive process of acquiring a tomographic image is very small. In particular, the method of this embodiment is extremely advantageous for applications in which many slices are repeatedly imaged to obtain a three-dimensional volume image. In addition to the fact that the repetition does not require the processing of section A, the discrete Radon transform S126 to imaging step S134 of section B are suitable for many-core processors such as general-purpose computing on graphics processing units (GPGPU), and therefore, the processing speed can be expected to increase in the future.

In addition, the oversampled system matrix $W_{OS}$ 212, the square system matrix $W_{SQ}$, and the inverse system matrix $W_{SQ}^{-1}$, all of which reflect the geometric aspect, are only in section A of the process from the system matrix generation step S112 to the discrete inverse Radon transform matrix calculation step S116. These are separated from section B for measurement (FIG. 4). This essentially separates the problem of convergence when using iteration for algebraic methods and the noise aspect for measurement. As a result, this embodiment also has the advantage that the phenomenon caused by approximate solutions that are unrelated to noise is less likely to occur, and various noise reduction processes commonly employed in image processing are more likely to be effective as intended.

2-3. Determination of the Thinning Order to Give Regular Square System Matrix

As discussed above in the overview, the fact that the discrete Radon inverse matrix $W_{SQ}^{-1}$ is obtained as an inverse matrix of the square system matrix $W_{SQ}$ depends on the appropriateness of the decimation sequence {k}. The decimation sequence {k} is determined in the matrix decimation process S114. The matrix decimation process S114 of this embodiment is not limited as long as a regular square system matrix is obtained in the result, and the following two methods are given as examples.

2-3-1. Random Selection Algorithm Based on Decision by Rank

FIG. 6A is a flowchart showing an example of a matrix decimation process in a randomized algorithm that employs random numbers or random selection. The total number of rows in the oversampled system matrix $W_{OS}$ 212 is N×(N+n) (FIG. 5). Of these, the number of rows left to make the matrix a square matrix is N×N, and the total number of rows to be decimated is N×n. From the range [1, N×(N+n)] of integers in the index that identifies the rows (row number), we determine the sequences of either N×N to keep or N×n to remove. For this determination, a randomized selection approach is adopted in FIG. 6A. That is to say, if either N×N units to keep or N×n units to remove are randomly determined by the random numbers generated, the decimation sequence {k} can be finally determined (S114-2). Once the decimation sequence {k} is determined, the square system matrix $W_{SQ}$ can be obtained from the oversampled system matrix $W_{OS}$ 212 by a corresponding decimation process (S114-4). Next, the rank is calculated for the square system matrix $W_{SQ}$ obtained (S114-6). The calculated rank is the same value as N × N if the square system matrix $W_{SQ}$ is regular, otherwise it is smaller than N×N. Therefore, the rank value serves as a reference to determine whether the square system matrix $W_{SQ}$ can have an inverse matrix or not. If the judgment shows that the rank is equal to N×N (S114-8, branch Y), the sequence {k} that gives the square system matrix $W_{SQ}$ at that point in time is output as it is to the decimation sequence storage unit 30, and the square system matrix $W_{SQ}$ 214 is output to the square system matrix storage unit 60 (S114-10). This concludes the process of matrix decimation. If the rank does not match N×N (S114-8, branch N), it is executed again from the selection of the decimation sequence {k} by a randomized algorithm based on another random number from S114-2 again (retry process). If such random selection algorithm is adopted, the matrix decimation process S114 can be executed at a practical speed. As will be explained later, the probability of obtaining a regular square system matrix $W_{SQ}$ when a randomized selection is made is affected by the selection of the value of the resolution N and the value of the oversampling amount n. When the resolution N is about 1000, the square system matrix $W_{SQ}$ can be obtained with sufficiently high probability even if n is about 1-2% of the resolution N or 10 to 20.

2-3-2. Gram-Schmidt's orthogonalization method

FIG. 6B is a flowchart showing an example of a matrix decimation process using Gram-Schmidt's orthogonalization. In the case of adopting the Gram-Schmidt orthogonalization method, the diagonalization process of the oversampled system matrix $W_{OS}$ is first performed (S114-12). The decimation sequence {k} is determined accordingly. The diagonalization can be performed by the QR decomposition method, for example. Each component of the corresponding first vector 228 also needs to be transformed, or mixed, by the diagonalization process. For this purpose, along with the decimation sequence {k} to be determined, the matrix data that defines this transformation is also determined. After the diagonalization, the Gram-Schmidt orthogonalization method (S114-14) can be performed to determine a group of linearly independent N×N row vectors from the oversampled system matrix $W_{OS}$ 212. This group of row vectors can be arranged to form the square system matrix $W_{SQ}$. At that time, the decimation sequence {k}, the square system matrix $W_{SQ}$, and a transformation matrix that mixes the components due to diagonalization are output (S114-16). The transformation matrix is used to transform the first vector 228 in the vector decimation process S130.

2-4. Confirmation of the Ratio Having Inverse (Existence Ratio of Solutions)

We now explain the success rate that the square system matrix $W_{SQ}$ with inverse matrices investigated by numerical simulation. Table 2 summarizes the ratio of N×N, or solution existence ratio, when the square system matrix $W_{SQ}$ is determined by preparing the oversampled system matrix $W_{OS}$ 212 and determining its rank by performing 20 matrix decimation processes, each following the random selection algorithm of FIG. 6A, to find the square system matrix $W_{SQ}$. To investigate how the solution existence ratio depends on N and the oversampling amount n, we investigated here across combinations where N=32, 30, and 28 and the oversampling amount n=0 to 10.

TABLE 2

| n | N = 32 | N = 30 | N = 28 |
|---|--------|--------|--------|
| 0 | 0.0 | 0.0 | 0.0 |
| 1 | 0.7 | 0.5 | 0.6 |
| 2 | 0.0 | 1.0 | 0.0 |
| 3 | 1.0 | 1.0 | 1.0 |
| 4 | 1.0 | 0.0 | 1.0 |
| 5 | 1.0 | 1.0 | 1.0 |
| 6 | 1.0 | 1.0 | 1.0 |
| 7 | 1.0 | 1.0 | 1.0 |
| 8 | 1.0 | 0.0 | 1.0 |
| 9 | 1.0 | 1.0 | 1.0 |
| 10 | 0.05 | 1.0 | 1.0 |

The values of the solution existence ratios shown in Table 2 become measures for the success rate of the square system matrix $W_{SQ}$ with a rank of N×N in the situation of running the random selection algorithm of FIG. 6A for the real oversampled system matrix $W_{OS}$ 212 with the same N and n adopted. As shown in Table 2, in general, as we increase the oversampling amount n, the solution existence ratio increases, and indeed, the value of the ratio increases rapidly up to about n=3. However, when we examine the tendency for each of these values of n, the solution existence ratio does not increase monotonically with respect to n. For example, for some even numbers (n=2, 4, 8, 10), the solution existence ratios are 0 or very small. The reason for this is not clear at present, but we expect that it is due to the fact that the symmetry increases when N is even and n is also even. Although the system matrix is smaller in size than actually adopted N, the existence ratio of the solution is sufficiently high even when N=128, which will be described later, and the same tendency is expected to be realized when N=1000. Although we have not been able to specify how much oversampling amount n is appropriate, the dependence on oversampling amount n is affected by changing N in Table 2. For this reason, it is also useful to adjust the resolution N as necessary in addition to the oversampling amount n. The resolution N can be easily reduced by, for example, intentionally not using detection elements located at either or both ends in the detection device, and correspondingly not using pixels at the periphery of the tomogram image.

2-5. Decimation by Block

The decimation for obtaining a regular square system matrix $W_{SQ}$ in this embodiment can also be performed by another method. The inventor has confirmed that a regular square system matrix $W_{SQ}$ can also be obtained by decimation of oversampled system matrices $W_{OS}$ by block that is grouped based on identical detection direction.

Figure 7A:
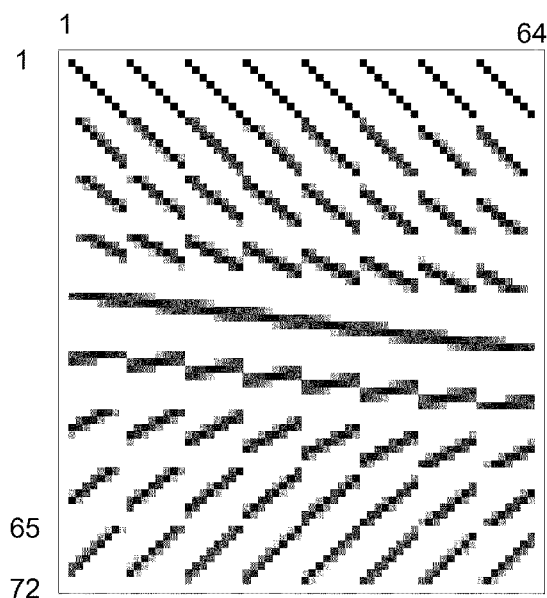
FIGS. 7A to 7B indicate explanatory diagrams indicating a decimation process by block according in an embodiment of the present disclosure.
Figure 7B:
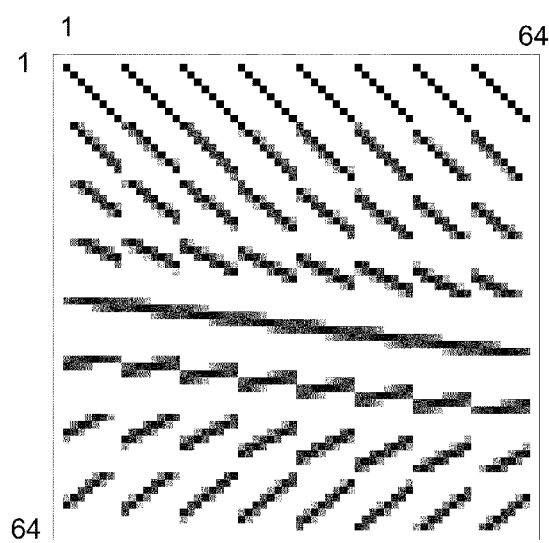

FIGS. 7A to 7B illustrate the decimation process by block in an example with a resolution N of 8 and an oversampling volume n of 1. FIG. 7A shows the oversampled system matrix $W_{OS}$ with images, where the number 0 is shown in white, the number 1 is shown in black, and their intermediate values are represented by the corresponding gray levels of lightness. This value is determined by the beam width τ, the width of the pixel δ and the geometric arrangement, as shown in FIG. 3. FIG. 7B shows the square system matrix $W_{SQ}$ obtained from the oversampled system matrix $W_{OS}$ via the decimation process by blocks in the same way.

The oversampled system matrix $W_{OS}$, which represents the contribution of absorption at each pixel location for each beam, is 72 rows by 64 columns when the resolution N is 8 and the oversampling amount n is 1. This corresponds to the fact that in FIG. 3, the resolution N has 8×8 pixels and the detection device 20 has 8 detection elements 22. Here, for the purpose of explanation, the origin of θ will be selected in a direction where the origin of θ is aligned with either the horizontal direction of the pixel sequence (left and right direction on the paper) or the vertical direction (same, up and down direction). In this section, as an example, the origin of θ (=0°) is the detection direction in which the beam 4 heads in the 12 o'clock direction on the paper surface. In this case, the submatrix of the first to eighth rows of the oversampled system matrix $W_{OS}$ in FIG. 7A is a numerical representation of the contribution made by each pixel to each detection element 22 when the detection direction θ is set to 0°. The submatrix of the oversampled system matrix $W_{OS}$, rows 9-16, is the contribution of each pixel to each detection element 22 when the detection direction θ is set to 20°. Likewise, the sub-matrices of rows 19-24, 25-32, . . . , and 65-72 are the same for the detection directions of 40°, 60°, . . . , and 160°, in that order. Thus, FIG. 7A is an oversampled system matrix $W_{OS}$ representing the contributions for each of the nine detection directions in total.

The elements of the oversampled system matrix $W_{OS}$ are described in detail. The submatrix of the first to eighth rows of the oversampled system matrix $W_{OS}$ is the contribution of each of the 8×8 pixels for each of the 8 detection elements 22 when the detection direction of the detection device 20 is at the origin (θ=0°). The elements of the first through 64th columns of the oversampled system matrix $W_{OS}$ also show the contribution of each of the 8×8 pixels in columns 1 through 8 for the 8 pixels in the first row of pixels, columns 9 through 16 for the 8 pixels in the second row of pixels, . . . , and column 57 through 64 for the 8 pixels in the eighth row of pixels.

The submatrix in rows 9-16 of the oversampled system matrix $W_{OS}$ is the numerical value of the contribution of each pixel for the case in which θ is directed in the detection direction of the next sampling detection direction of the origin (=)20°. This value is also the contribution that each pixel provides to each detection element 22 in that detection direction. The same applies for the submatrix in row 17 and thereafter. In the case of the general detection direction θ, the contribution of each pixel can have an intermediate value. For example, it depends on the geometric arrangement of how much of the area δ2 of one pixel is passed by each beam of width τ.

The decimation process by block of this embodiment, if explained in accordance with the example of FIGS. 7A to 7B, is to remove the submatrix of the 65th to 72nd row of the oversampled system matrix $W_{OS}$, for example, to make it a square matrix with 64 rows and 64 columns. This is equivalent to making the decimation sequence {k} a sequence of 8 elements starting at 65, i.e., 65, 66, . . . , 72. More generally, the oversampling amount n x resolution N elements to be removed from the oversampled system matrix $W_{OS}$ in the decimation process can be a successive range of a clustered block. Furthermore, the successive range can be 1, N+1, 2×N+1, . . . , N×N+1, i.e., starting with (s−1)×N+1, where s is an integer greater than or equal to 1. The decimation process can also be performed by determining N×N elements to keep in the oversampled system matrix $W_{OS}$ by indirectly identifying the remaining n×N elements. The N×N elements to keep in that case shall be of a successive range ending in s×N, with s as an integer greater than or equal to 1. In this case, the block of the range of rows to remove from the oversampled system matrix $W_{OS}$ when the oversampling amount n is greater than or equal to 2 may be divided into two blocks, one block containing the first row and another block containing the (N+n)×N rows (the last row). In any case, the submatrix that is the block of the range of rows to be removed is not only a successive range, but also a unit of the detection direction.

In the decimation process, the square system matrix $W_{SQ}$ does not necessarily become a regular in the process of removing or keeping a successive range. If the square systems matrix $W_{SQ}$ becomes regular, it is enough to perform the process once, but if it does not become regular, the process is executed again until it becomes regular by changing the condition. The condition is changed, for example, by changing the value of the integer s.

Figure 8A:
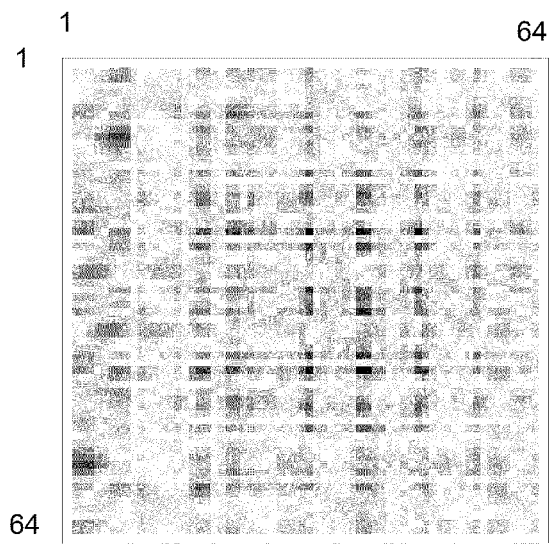
FIGS. 8A to 8B illustrate explanatory diagrams indicating the performance of a decimation process by block in an embodiment of the present disclosure.
Figure 8B:
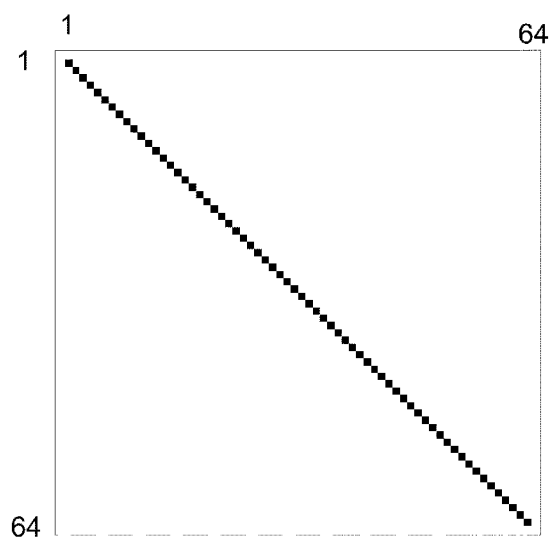

FIGS. 8A to 8B indicate the results of the decimation process by block in this embodiment. FIG. 8A shows the discrete Radon inverse matrix $W_{SQ}^{-1}$, which is an inverse matrix calculated from the square system matrix $W_{SQ}$ of FIG. 7B, and FIG. 8B shows a matrix obtained by operating from the left the discrete Radon inverse matrix $W_{SQ}^{-1}$ to the square system matrix $W_{SQ}$. That the square system matrix $W_{SQ}$ in FIG. 7B actually has the discrete Radon inverse matrix $W_{SQ}^{-1}$ for its inverse is evident in the fact that the matrix shown in FIG. 8B is an identity matrix.

Apart from the case of resolution N=8 and oversampling amount of 1, the inventor confirmed that it is possible to obtain a regular square system matrix $W_{SQ}$ by decimation process with a successive range of blocks corresponding to the last detection direction in the case of oversampling amount of 1 with N=2 and N=64, respectively.

The explanations based on FIGS. 4 and 5 are also equally valid for the decimation process by blocks by a successive range. In particular, as can be seen from FIG. 5, when the decimation sequence {k} is one for removing a successive range or one for keeping a successive range, the detection direction corresponding to the range to remove or the range to keep can be identified in the present embodiment. For example, in FIGS. 7A to 7B, the 65th to 72nd rows of the oversampled system matrix $W_{OS}$ are removed, and the elements corresponding to the 160° detection direction are removed. Correspondingly, the measurements acquired in the 160° detection direction in the detection operation are also removed according to the decimation sequence {k}. In other words, when the decimation process by block is performed in this embodiment, the detection process itself can be omitted for the detection direction corresponding to the n×N elements that specify the range to remove in the decimation sequence {k}. As a consequence, in the detection operation, among the (N+n) directions by oversampling, the n directions can be omitted, and thus the minimum detection direction is the N directions, in which case the decimation process is substantially not required.

2-6. Summary of Specific Structure

As shown above, the combination of oversampling and decimation (thinning) process used in this embodiment provides significant practicality in the process of capturing and acquiring of tomographic images. One of the advantages of this method is that the process of determining the decimation sequence {k} can be performed separately from the process of the user's tomographic image capturing, and therefore, it is not necessary to repeat the process for an iterative approximation, which is very computationally intensive.

3. Implementation of the Embodiment

The present embodiment can be implemented as a tomographic imaging device or as control and processing software for an existing tomographic imaging apparatus.

3-1. Implementation on Tomographic Imaging Devices

The tomographic imaging device 100 of the present embodiment can produce tomographic images of comparable or better quality than those with conventional ART in a conventional tomographic imaging device by performing the above-described processing mainly in the control device 150. The computational resources required for this process are also sufficiently practical and the processing is very fast.

Figure 9:
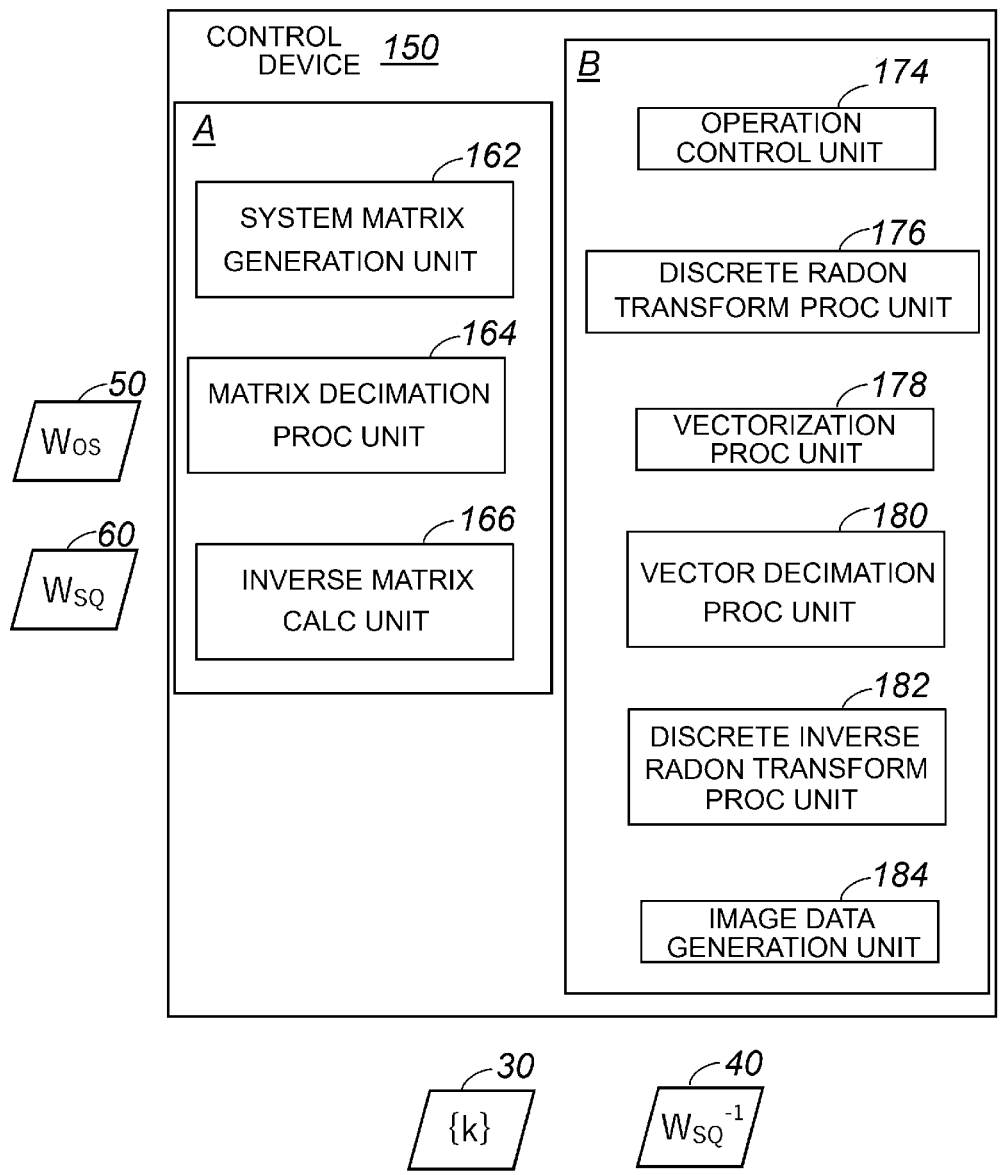
FIG. 9 is a block diagram indicating a specific functional unit and a specific data storage unit of a control device in the tomographic imaging device implementation of the present embodiment.

FIG. 9 is a block diagram showing some unique functional units and unique data storage units of the control device 150 in the case of implementing the present embodiment with a tomographic imaging device. The system matrix generation unit 162, the matrix decimation processing unit 164, and the inverse matrix calculation unit 166 perform the system matrix generation step S112, the matrix decimation processing S114, and the discrete inverse Radon transform matrix calculation step S116, respectively. Similarly, the operation control unit 174, the discrete Radon conversion processing unit 176, the vectorization processing unit 178, the vector decimation processing unit 180, the discrete inverse Radon transform processing unit 182, and the image data generation unit 184 perform the irradiation and detection step S124, the discrete Radon transform S126, the vectorization S128, the vector decimation process S130, the discrete inverse Radon transform process S132, and the imaging step S134, respectively. In its operation, the decimation sequence storage unit 30, the discrete inverse Radon transform matrix storage unit 40, the oversampled system matrix storage unit 50, and the square system matrix storage unit 60 are also utilized. In addition, the irradiation and detection step S124, the discrete Radon transform S126, and the vectorization S128 can be performed by a functional unit that may functionally perform a combination of these processes, just as the irradiation and detection S124 to the vectorization S128 can be performed with equivalent series of processes. Furthermore, the control device 150 can be implemented in various forms, such as for mainly processing of section A, or on the contrary, for mainly processing of section B, as needed, as the functional units required for processing of section A and for processing of section B are clearly separated. Specific examples of tomographic imaging devices include X-ray CT scanners, single photon emission computed tomography (SPECT), optical tomography, and optical CT devices.

3-2. Implementation in Computer Program

The entirety of the system can be implemented as the tomographic imaging device 100 with a tomographic imaging device equipped with an emission device 10 and a detection device 20 as an implementation of a computer program for example, in which the control device 150 in the tomographic imaging device 100 performs part of or all of the control steps, conversions, calculations, and other computational processes. Furthermore, the control device 150 in the tomographic imaging device 100 in the present embodiment can be made to perform only the processes in section B (FIG. 4) at the time when the user captures the tomographic images.

4. Verification by Computer Simulation (Example)

Figure 10A:
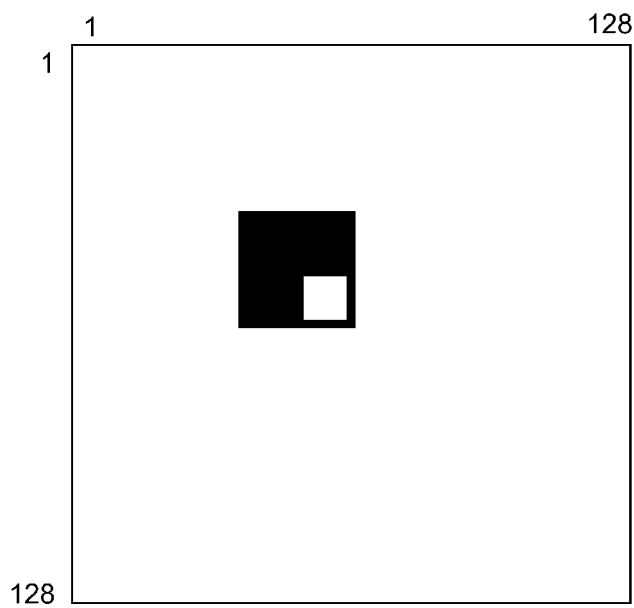
FIGS. 10A to 10B indicate diagrams indicating verification data, or numerical phantom, used for verification in an example for an embodiment of the present disclosure (FIG. 10A) and a corresponding oversampled sinogram (FIG. 10B).
Figure 10B:
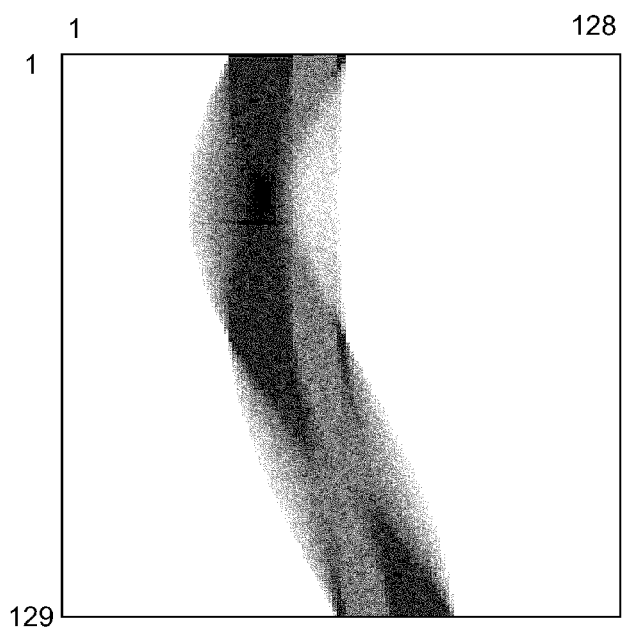

The effectiveness of the reconstruction method according to the present embodiment was confirmed by computer simulation. The general processing, including the inverse Radon transform, including those of conventional methods for contrast, was performed using the mathematical processing software Mathematica (Wolfram Research, Inc., Champaign, Illinois) and the image processing software ImageJ (U.S. National Institutes of Health). A computer with an Intel Xeon E5 processor (3.5 GHz, 6-Core type) CPU and a 64 GB main memory was employed for the simulation process, including the processing of the control device 150 in this embodiment. FIGS. 10A to 10B show the validation data (numerical phantoms) used for verification (FIG. 10A, referred to as an original image) and the corresponding oversampled sinogram (FIG. 10B). In each figure, solid lines are added to the periphery of the image to distinguish it from the background, and numerical values indicating the first and last pixel numbers representing the coordinates of the pixels are shown on the top and left sides. The original image (numerical phantom) is numerical data artificially given for simulating the structure of attenuation rate in a cross section of an object in a computer simulation, and can be represented as N=128, or 128×128 image with pixels corresponding to spatial positions. In FIG. 10A, the region of strong absorption is depicted darkly and the region of weak absorption is depicted brightly. In the computer simulation, the operation of the irradiation and detection S124 by the tomographic imaging device 100 was also simulated, and numerical data corresponding to the measured values were obtained by calculation. In the oversampled sinogram representing the above, the low value of detection intensity is darkened and the high value is lightened. The oversample sinogram in FIG. 10B was obtained based on the discrete Radon transform S126 (FIG. 4), which corresponds to the measurement operation. Specifically, the oversampling discrete Radon transform is performed by a detection device 20 having 128 detection elements 22 with N=128 for a projection from 129 (=N+n) directions with n=1 adopted. To reflect this, the oversampled syinogram in FIG. 10B is displayed as an image with a size of 128×129 pixels. The oversampled sinogram in FIG. 10B is for the operation of this embodiment, however, it is also used for the processing of conventional FBP and ML-EM methods. In conventional methods, oversampling is not particularly necessary and a sinogram acquired in the N directions (128 directions) can be employed (not shown), however, for a more direct comparison, an oversampled sinogram for the (N+n) directions is adopted for the present embodiment and the conventional one.

As a validation of the present embodiment, the reconstructed images were acquired by implementing the processes shown in FIG. 5 and FIG. 6A. The process employed to determine the decimation sequence {k} of the matrix decimation process S114 is the randomized selection algorithm shown in FIG. 6A. When the process of determining the decimation sequence {k} based on the algorithm was actually carried out many times, in cases the rank did not match (or reach) N×N (128×128) in the decimation process S114-8, as shown in the branch N, and returned to the decision S114-2 by the random number, which required retry process. The actual rate of retry process required to reflect the existence ratio of solutions was only 3 to 4 retries for 20 algorithmic operations, and for the remaining 16 to 17 retries one run of decision S114-2 with random numbers was sufficient.

Figure 11A:
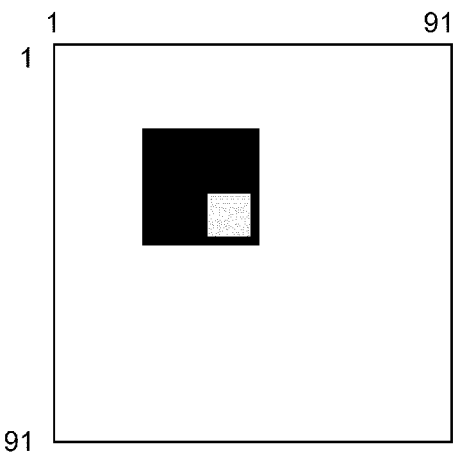
FIGS. 11A to 11D indicate reconstructed images obtained in an embodiment of the present disclosure (FIG. 11A), in a case where a HANN filter is adopted in a conventional FBP method (FIG. 11B), and for a conventional algebraic reconstruction method in which 30-repetition of iterative approximation calculation (ML-EM method) in conventional algebraic reconstruction (FIG. 11C). In addition.
Figure 11B:
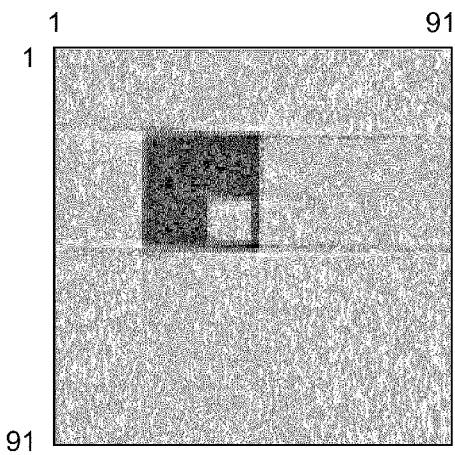
Figure 11C:
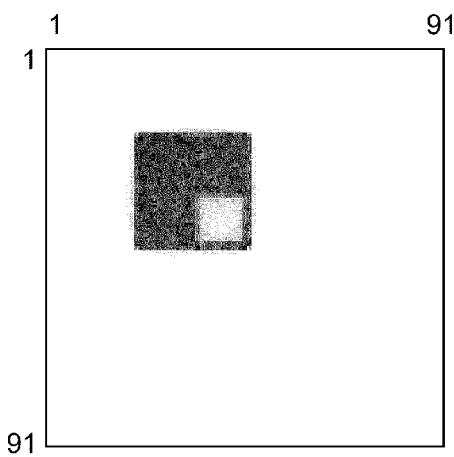

The reconstructed images shown in FIGS. 11A to 11D were obtained with the present embodiment (FIG. 11A), with a Hann filter in the conventional FBP method (FIG. 11B), and by performing iterative approximation calculations (ML-EM method) 30 times as a conventional algebraic reconstruction method (FIG. 11C). Although the reconstructed images in this embodiment are obtained in the area of 128×128 pixels, these reconstructed images are shown only in the area of 91×91 pixels. This is because the area where the reconstructed image can be obtained by simulation using the FBP method is a circular area with a diameter of 128 pixels, and a square area roughly inscribed in the circle can be compared.

As it is clear by comparing FIGS. 10A and 11A, the reconstructed images with extremely high reproducibility were obtained in this embodiment. Such high reproducibility was true for any decimation sequences {k} obtained by randomized selection algorithm with or without retry processing. This is an advantage of this embodiment, which is supported by the fact that the discrete Radon inverse matrix $W_{SQ}^{-1}$ is an algebraic exact solution, unlike the conventional Hann filtered FBP method (FIG. 11B) and the ML-EM method (FIG. 11C), and this advantage is also confirmed through the high reproducibility of the images themselves.

Next, a comparison of the reproducibility of the reconstructed images was performed based on a numerical measure. Specifically, the reproducibility of each reconstructed image was evaluated using the ISNR (Improvement in Signal-to-Noise ratio) in Formula (3).

Math 1

$$ISNR = 10\log_{10}\left(\frac{\|\tilde{x} - x\|^2}{\|\hat{x} - x\|^2}\right) \quad (3)$$

Figure 11D:
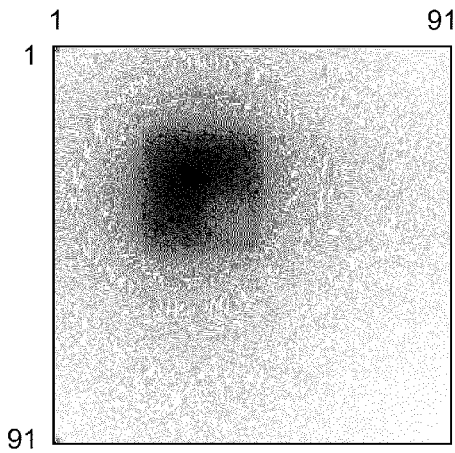

Here,

Math 2

$$x, \hat{x}, \tilde{x}$$

are vector representations of the original image shown in FIG. 10A, the reconstructed image of either of the target FIGS. 11A-11C, and the reconstructed image of the simple inverse Radon transform (back projection without filters), respectively. The reconstructed image of the simple inverse Radon transformation whose image is shown in FIG. 11D is a reference for comparison. The evaluated values of Formula (3) were for the 91×91 pixel ranges shown in FIGS. 11A-11D. The INSR values of the reconstructed images of the reconstructed images in FIGS. 11A-11C, which were obtained based on the reconstructed images of the simple inverse Radon transform, are shown in Table 3.

TABLE 3

| | This Embodiment (FIG. 11A) | FBP + Hann Filter (FIG. 11B) | ML-EM (FIG. 11C) |
| --- | --- | --- | --- |
| ISNR[dB] | 221.001 | 42.1208 | 52.9420 |

From each ISNR value, it was quantitatively confirmed that the reproducibility of the reconstructed images by the present embodiment was greatly enhanced compared to the conventional cases using the FBP method and the iterative approximate reconstruction method.

5. Variations in Image Reconstruction Methods

In the image reconstruction method described above, the image reconstruction was performed by actually calculating the inverse matrix $W_{SQ}^{-1}$ from the regular square system matrix $W_{SQ}$ under a guarantee that the square system matrix $W_{SQ}$ obtained from the oversampled system matrix $W_{OS}$ is regular and has an inverse matrix. In the present disclosure, image reconstruction can also be performed using the pseudo-inverse of a similar regular square system matrix $W_{SQ}$ as an additional image reconstruction method.

The pseudo-inverse matrix for this additional image reconstruction method is calculated, for example, by a singular value decomposition (SVD) technique. For example, a Moore-Penrose type inverse matrix can be generated by singular value decomposition for a square matrix and is an example of a useful pseudo-inverse matrix for this additional image reconstruction method.

In embodiments of the present disclosure, Formula (4), corresponding to Eq. (1), is utilized in both the image reconstruction method described above and this additional image reconstruction method.

$$X' = W_{SQ} X \quad (4)$$

In this case, it is guaranteed that the square system matrix $W_{SQ}$ is regular, i.e., it has an inverse matrix. The image reconstruction method described above was to obtain the discrete Radon inverse matrix $W_{SQ}^{-1}$, which is the inverse of the regular square system matrix $W_{SQ}$, and to reconstruct the image according to the Formula (5).

$$X = W_{SQ}^{-1} X' \quad (5)$$

In this additional image reconstruction method, although Formulas are equivalent until Formula (4), $$X = W_p^{-1} X' \qquad (6)$$

is performed in place of Formula (5) for image reconstruction. Here, $W_p^{-1}$ is the pseudo-inverse of the square system matrix $W_{SQ}$. In other words, the image reconstruction can be performed in this additional image reconstruction method even if the pseudo-inverse matrix $W_p^{-1}$, which is an approximate inverse matrix, is used instead of daring to use the inverse matrix of the square system matrix $W_{SQ}$, which is regular and the existence of the inverse matrix is guaranteed. In the following, we will describe a case where reconstruction was performed using X-ray CT data (FIGS. 12A to 12E and FIG. 13A to 13K) and a case where reconstruction was performed using neutron ray CT data (FIGS. 14A to 14E and FIG. 15A to 15J).

Figure 12A:
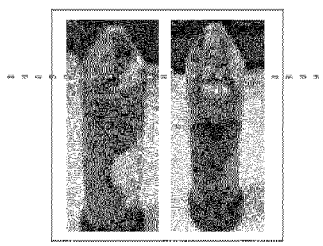
FIGS. 12A to 12E indicate explanatory illustrations of an example reconstruction based on data of an X-ray CT acquired from a mouse sample regarding the additional reconstruction in an embodiment of the present disclosure.
Figure 12B:
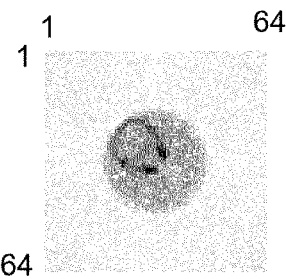
Figure 12C:
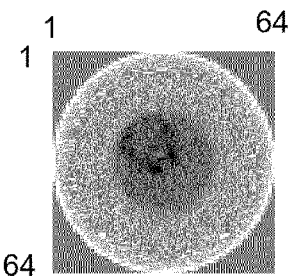
Figure 12D:
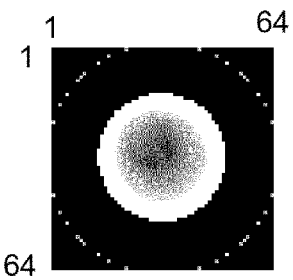
Figure 12E:
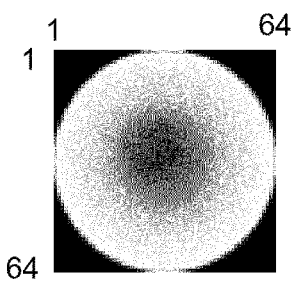

FIGS. 12A to 12E illustrate a case where reconstruction processing was performed using actual X-ray CT data acquired using a mouse specimen, FIG. 12A is a photograph of a mouse specimen, FIG. 12B is a reconstructed image using the pseudo-inverse matrix $W_p^{-1}$, FIG. 12C is a reconstructed image with FBP for comparison, FIG. 12D is a reconstructed image with ML-EM for comparison, and FIG. 12E is a reconstructed image with a simple inverse Radon transform for comparison. The specimen in FIG. 12A were imaged by an X-ray CT system (SCANXMATE-E090S, ComScan Techno Co.LTD., Yokohama, Japan). The captured data were acquired with a small number of pixels (256×130), which is different from its original performance but suitable for comparative calculations, and were coarse-grained to 64×64, i.e., N=64, at the time of reconstruction.

The process for FIG. 12B of this additional image reconstruction method is described with the elements in FIG. 4 added as necessary. After calculating the oversampled system matrix $W_{OS}$ for the detection direction of 65 directions in intervals of 180°/65, i.e., 2.769° (FIG. 4, S112), the first direction is set to 0° and conducting the matrix decimation process by block with a sequential range corresponding to the 65th 177.230° detection direction to determine the square system matrix $W_{SQ}$, thereby determining the square system matrix $W_{SQ}$ with a sequential range of elements corresponding to the 64 directions (S114). This determines the decimation sequence {k}. The regularity of this square system matrix $W_{SQ}$ is confirmed by the fact that the rank is 4096 (=64×64). Furthermore, the pseudo-inverse matrix $W_p^{-1}$ was calculated by the Moore Penrose type inverse of the square system matrix $W_{SQ}$ at issue, which was used as the discrete Radon inverse matrix $W_{SQ}^{-1}$. Thus, in FIG. 4, the pseudo-inverse matrix is calculated in the discrete Radon Inverse Matrix calculation step S116, and the pseudo-inverse matrix is stored in the discrete inverse Radon transform matrix storage unit 40 (FIG. 4, FIG. 5).

Next, data were acquired from 130 directions in 360°/130, i.e., intervals of 2.769°, corresponding to the above 65 detection directions for the mouse sample. In this case, the number of detectors is 256. For the 256×130 sinogram image obtained here, the data was trimmed to keep the 1st to 65th rows corresponding to 180°, and the image size was reduced by 25% for 256 pixels in the detector direction (S122, S124). This example shows that our method is also effective for data processed in this way. The first vector $X_{OS}'$ corresponding to the oversampled sinogram was generated (S126, S128). Next, a vector decimation process (S130) was performed to obtain the second vector X' by decimating the components of the detection direction 177.230°, which is the 65th direction, or 65th based on the decimation sequence {k}, and the second vector X' was obtained by performing a vector decimation process (S130). The third vector X was calculated by using the pseudo-inverse matrix $W_p^{-1}$ for the discrete Radon inverse matrix $W_{SQ}^{-1}$ (S132), and the reconstructed image was further obtained by the de-vectorization process (S134). The calculation of the pseudo-inverse matrix $W_p^{-1}$ was performed with the tolerance set to 1/19, which will be described below.

For FIGS. 12C to 12E, we used data acquired from 64 directions of detection at 180°/64, i.e., intervals of 2.8125° and resized the sinogram images to be similar in size to the case of FIG. 12B. FIGS. 12C to 12E were obtained using ImageJ (National Institutes of Health, USA), and the reconstructed images were obtained by FBP processing as in FIG. 12C, ML-EM processing (number of iterations: 1) in FIG. 12D, and BP processing in FIG. 12E. The relationship between the number of iterations and image quality in ML-EM processing was investigated beforehand, and it was confirmed that one iteration was the best.

It is evident from FIGS. 12B-12E that the additional image reconstruction method using the pseudo-inverse matrix $W_p^{-1}$ can produce reconstructed images with good quality in comparison with FBP, ML-EM and BP.

Figure 13A:
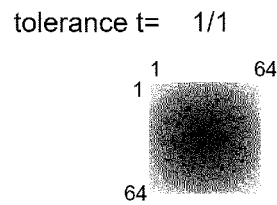
FIGS. 13A to 13J indicate reconstructed images generated by a pseudo-inverse matrix $W_p^{-1}$ in an additional image reconstruction method according to an embodiment of the present disclosure.
Figure 13B:
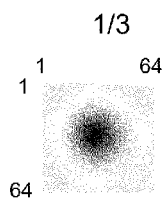
Figure 13C:
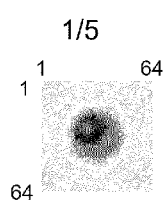
Figure 13D:
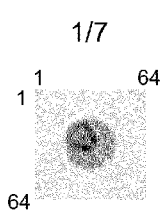
Figure 13E:
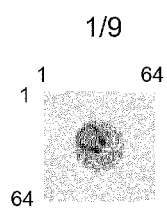
Figure 13F:
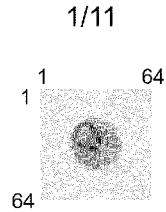
Figure 13G:
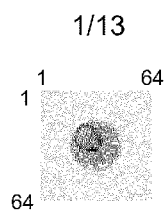
Figure 13H:
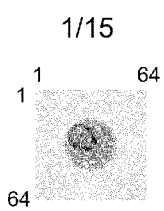
Figure 13I:
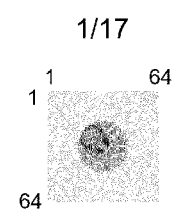
Figure 13J:
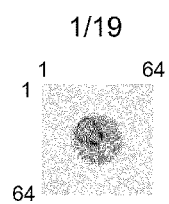
Figure 13K:
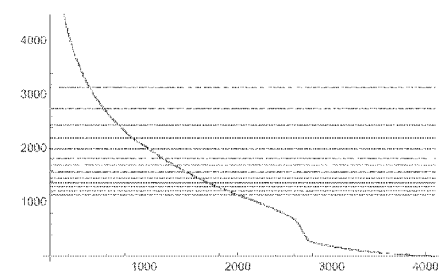
FIG. 13K is a graph in which singular values are arranged in order of magnitude.

The calculation of the pseudo-inverse matrix $W_p^{-1}$ is typically carried out by setting an appropriate tolerance value. The tolerance value is the ratio of a reference value for excluding singular values in the singular value sequence to the maximum singular value, in the process of generating a pseudo-inverse matrix through approximation of the singular value decomposition. For instance, if 1/5 is set as the tolerance value, the pseudo-inverse matrix is calculated from the singular value decomposed matrix by replacing any singular values that have a value less than 1/5 of the maximum singular value by 0. FIGS. 13A to 13J include the reconstructed images generated by the pseudo-inverse matrix $W_p^{-1}$ calculated by changing the tolerance, and FIGS. 13A to 13J show the images with the tolerance values set to ones indicated in each figure. FIG. 13K is a graph of singular values arranged in order of size, with the values of the singular values indicated on the vertical axis and the order on the horizontal axis. The graph is accompanied by a plurality of straight lines indicating a plurality of tolerance values. As can be seen from FIG. 13A, when the tolerance is set to 1/1, the reconstructed image does not produce a recognizable image. As the tolerance is reduced, the sharpness of the reconstructed image increases, but the reconstructed images are relatively stable after 1/13.

Figure 14A:
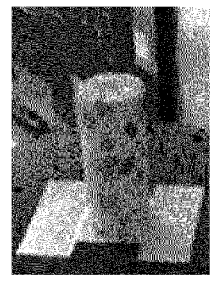
FIGS. 14A to 14E indicate explanatory illustrations of an example reconstruction based on data of a neutron beam CT acquired by using a concrete sample regarding the additional reconstruction in an embodiment of the present disclosure.
Figure 14B:
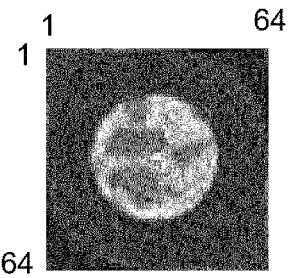
Figure 14C:
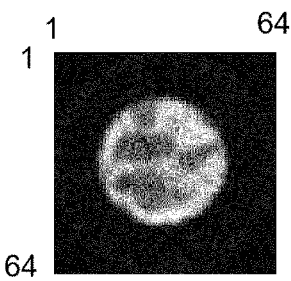
Figure 14D:
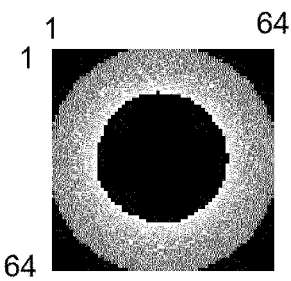
Figure 14E:
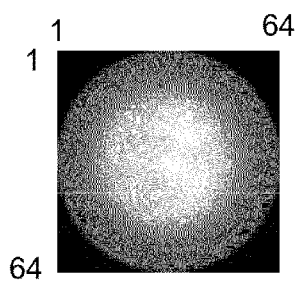
Figure 15A:
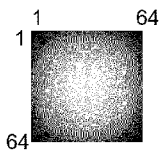
FIGS. 15A to 15J indicate reconstructed images generated by a pseudo-inverse matrix $W_p^{-1}$ in an additional image reconstruction method in an embodiment of the present disclosure.
Figure 15B:
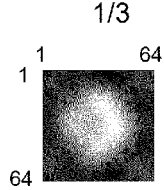
Figure 15C:
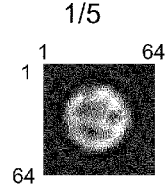
Figure 15D:
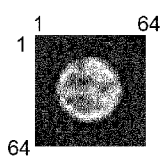
Figure 15E:
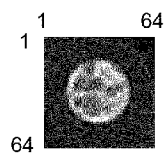
Figure 15F:
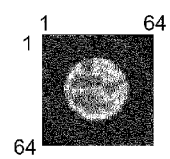
Figure 15G:
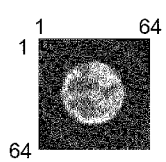
Figure 15H:
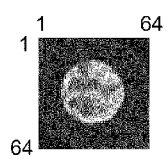
Figure 15I:
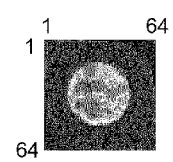
Figure 15J:
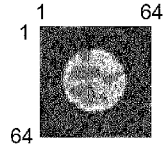

FIGS. 14A to 14E illustrate a case where the reconstruction process was performed on a concrete specimen (diameter 25 mm×height 60 mm, 70 g) using actual neutron-ray CT data; FIG. 14A is a photograph of the concrete specimen, FIG. 14B is the reconstructed image using the pseudo-inverse matrix $W_p^{-1}$, FIG. 14C is a reconstructed image by FBP for comparison, FIG. 14D is a reconstructed image by ML-EM for comparison, and FIG. 14E is a reconstructed image by simple inverse Radon transform for comparison. The specimen in FIG. 14A were imaged by a CT scanner by a small accelerator neutron beam sauce (RIKEN Accelerator-driven Neutron Source, RIKEN Neutron Beam Technology Development Team, RIKEN, Wako). The imaging data were acquired at 3° intervals of 120 steps over 360° and coarse-grained to 64×64, i.e., N=64, at the time of reconstruction.

The process for FIG. 14B of this additional image reconstruction method will be described, with the elements in FIG. 4 as necessary. After first calculating the oversampled system matrix $W_{OS}$ for the detection direction of 65 directions in intervals of 180°/65, i.e., 2.769° (FIG. 4, S112), the matrix decimation process was performed, with the first direction being 0°, by thinning out by block the elements of a successive range corresponding to the 65th 177.230° detection direction, for determining the square system matrix $W_{SQ}$ with the elements of a successive range corresponding to the 64 directions (S114). This determines the decimation sequence {k}. The regularity of this square system matrix $W_{SQ}$ was confirmed by the fact that the floor number was 4096 (=64×64). Furthermore, the pseudo-inverse matrix $W_p^{-1}$ was derived by calculating the Moore Penrose type inverse of the square system matrix $W_{SQ}$ in question, and it was used as the discrete Radon inverse matrix $W_{SQ}^{-1}$. Therefore, in FIG. 4, the pseudo-inverse matrix is calculated in the discrete Radon inversion matrix calculation step S116, and the pseudo-inverse matrix is stored in the discrete inverse Radon transform matrix storage unit 40 (FIG. 4 and FIG. 5).

Next, data were acquired from 120 directions in 360°/120, i.e., intervals of 3°, corresponding to that of the above-mentioned 65 detection directions for a concrete specimen. For the sinogram image obtained for the 120 directions, the image was trimmed so that lines 1 to 60 corresponding to 180° were retained, and the image was resized and expanded to 65 directions (S122, S124). This example shows that our method is also effective for the data processed in this way. The first vector Xos' corresponding to the oversampled sinogram was generated (S126, S128). Next, a vector decimation process (S130) was performed to obtain the second vector X' by decimating the components of the detection direction 177.230°, which is the 65th direction of 65 directions based on the decimation sequence {k}. The third vector X was calculated by using the pseudo-inverse matrix $W_p^{-1}$ for the discrete Radon inverse matrix $W_{SQ}^{-1}$ (S132), and the reconstructed image was further obtained by the devectorization process (S134). The calculation of the pseudo-inverse matrix $W_p^{-1}$ was performed with the tolerance set to 1/19, which will be described below.

For FIGS. 14C-14E, we used data acquired from 120 detection directions in 360°/120, i.e., 3° intervals, and resized their sinogram images to be the same size as in FIG. 14B. FIGS. 14C-14E were obtained by ImageJ, the reconstructed images were obtained by FBP processing for FIG. 14C, ML-EM processing for FIG. 14D (number of iterations: 1), and BP processing for FIG. 14E.

As is clear from FIGS. 14B-14E, we confirmed that the additional image reconstruction method using the pseudo-inverse matrix $W_p^{-1}$ was able to obtain reconstructed images with good quality in comparison with FBP, ML-EM, and BP.

Moreover, FIGS. 15A to 15J include reconstructed images generated by the pseudo-inverse matrix $W_p^{-1}$ calculated by changing the tolerance, and FIGS. 15A to 15J show the images with tolerance values set to ones indicated in each figure. As can be seen from FIG. 15A, even in the case of neutron CT, the reconstructed image does not produce a recognizable image when the tolerance is set to 1/1. As the tolerance is reduced, the sharpness of the reconstructed image increases, but the reconstructed image is relatively stable after 1/13.

Figure 16A:
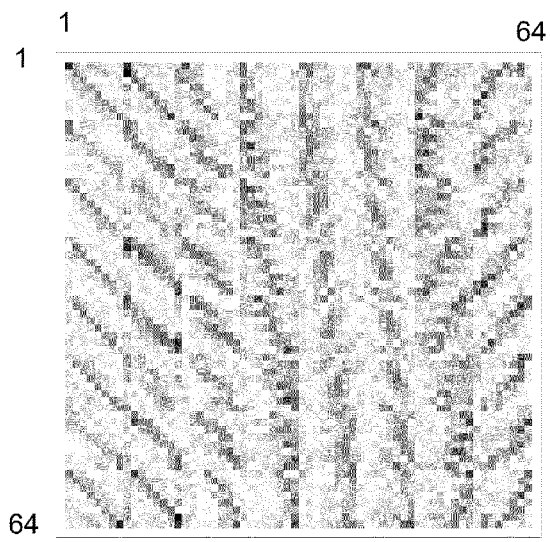
FIGS. 16A to 16B illustrate examples of a pseudo-inverse matrix $W_p^{-1}$ in an additional image reconstruction method in an embodiment of the present disclosure.
Figure 16B:
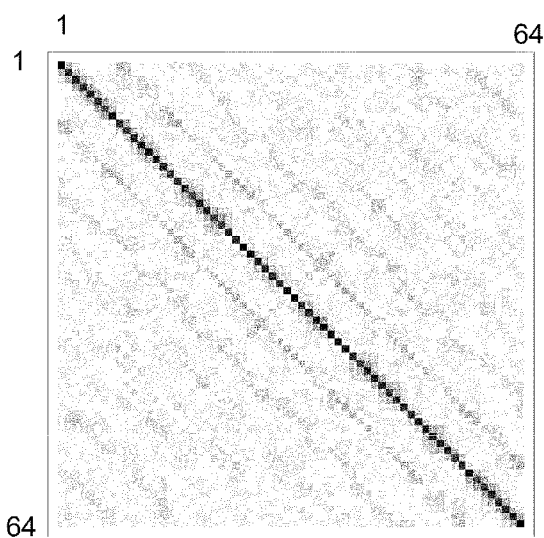

FIGS. 16A to 16B include examples of pseudo-inverse matrices $W_p^{-1}$ in this additional image reconstruction method, where FIG. 16A indicates the pseudo-inverse matrix $W_p^{-1}$ obtained for the square system matrix $W_{SQ}$ in FIG. 7B, whereas FIG. 16B indicates the matrix obtained by operating the pseudo-inverse matrix $W_p^{-1}$ on the square system matrix $W_{SQ}$ from the left. From the comparison between FIG. 8A and FIG. 16A, the pseudo-inverse matrix $W_p^{-1}$ does not match the discrete Radon inverse matrix $W_{SQ}^{-1}$, even if they are calculated for an identical square system matrix $W_{SQ}$. Even in that case, based on the comparison between FIG. 8B and FIG. 16B, if we look only at the outcome of operating the inverse matrix $W_p^{-1}$ to the square system matrix $W_{SQ}$ from the left, a matrix that can be approximated to the identity matrix is calculated. This is also true when the inverse matrix $W_p^{-1}$ is operated on the square system matrix $W_{SQ}$ from the right (not shown).

As described above, we confirmed that the use of a pseudo-inverse matrix for the square system matrix $W_{SQ}$, which is guaranteed to be regular and has an inverse matrix, produces a reconstructed image of sufficient quality.

It should be noted that, in general, the smaller the tolerance value for the pseudo-inverse matrix, the closer the calculated pseudo-inverse matrix is to the inverse matrix and thus the resolution of the reconstructed image becomes higher. However, in measurements using a real-world measurement device, smaller tolerance values do not necessarily result in a good reconstructed image. This is because there are various disturbing factors that cannot be attributed to geometric factors. For example, factors such as noise in the detection signal, beam instability, beam scattering, and inherent imaging characteristics of the instrument itself still remain as disturbing factors in modern instruments. Normally, the imaging performance of the whole system, which reflects all these factors, is evaluated by, for example, the modulation transfer function (MTF), which indicates the resolution characteristics, and the Wiener spectrum, which is a measure of the image granularity. By using a predetermined tolerance value greater than 0 (e.g., 1/13 to 1/19 in FIGS. 13G-13J and FIGS. 15G-15J) in the present additional image reconstruction method, a filter operation to exclude disturbing factors other than geometric factors is achieved. Since this filter operation can be easily adjusted for its effect by increasing or decreasing the tolerance value, it can be useful in creating the necessary reconstruction image according to the image characteristics of interest, such as whether the resolution or the quantitative nature of the image is important.

6. Variations

This embodiment can be implemented in various forms other than those described above, regardless of whether it is implemented with a tomographic image data acquisition method, a tomographic image data acquisition device or a computer program for that purpose. For example, it is not required for the user to be involved in the process of determining the device parameter information in section A in FIGS. 4, 5, 7A, and 7B, and it is also easy to modify the embodiment in such a way that the user is involved only in obtaining the measurement information in section B. Furthermore, for example, when provided by a computer program for implementing the present embodiment, it is also possible to implement the present embodiment by adopting existing or already installed hardware for irradiation and detection and newly incorporating the above-mentioned processes into the computer program for controlling it. Thus, the method of this embodiment can be implemented through various modes of implementation.

In addition to the variations of the embodiment, another variation of the details of the process is also a part of this embodiment. One example of this is a method of determining the contribution of a pixel with respect to the beam 4 to a detection element 22 described with reference to FIG. 3. In addition to the method of using the area of the patterned area in FIG. 3 as the contribution, other practical methods may be employed in this embodiment as well. For example, instead of the area, it is also advantageous to have a weight depending on the length of the sweep, or to adopt Siddon's algorithm, which efficiently evaluates the length of the sweep, to determine the above contribution (Non-Patent Document 3). Furthermore, it is also advantageous to utilize the method of Sunnegardh and Danielson, which is capable of anti-aliasing to achieve a higher image quality (Non-Patent Document 4).

Furthermore, although the explanations from FIG. 3 and thereafter have been explained by the operation of one example tomographic imaging device 100, the present embodiment is not necessarily limited to ones employing the emission device 10. This embodiment can be similarly applied to other techniques such as SPECT (single-photon emission tomography), in which tomographic imaging of an object is performed without the use of an emission device.

In the above description, the embodiment of the present disclosure has been described specifically. Any description in this Specification is for the purpose of explaining the present disclosure, therefore the scope of the disclosure of this disclosure should be determined based on recitations of the claims. Furthermore, other variation based on any combination of the embodiment is included in the present disclosure, which variation should be also within a scope of the present disclosure.

INDUSTRIAL APPLICABILITY

The present disclosure can be applied to any tomographic imaging methods where the waves or particles are transmitted through an object itself, e.g., by, for example, being irradiated onto the object, such as X-ray CT scanners, Single Photon Emission Computed Tomography (SPECT), Optical Tomography, and optical CT devices.

REFERENCE SIGNS LIST

100 Tomographic imaging device (tomographic image data acquisition device) Object
  4 Beam
  10 Emission device
  20 Detection device
  22 Detection element
  30 Decimation sequence storage unit
  40 Discrete inverse Radon transform matrix storage unit
  50 Oversampled system matrix storage unit
  60 Square system matrix storage unit
  150 Control device
  162 System matrix generation unit
  164 Matrix decimation processing unit
  166 Inverse matrix calculation unit
  174 Operation control unit
  176 Discrete Radon conversion processing unit
  178 Vectorization processing unit
  180 Vector decimation processing unit
  182 Discrete inverse Radon transform processing unit
  184 Image data generation unit
  212 Oversampled system matrix $W_{OS}$
  214 Square system matrix $W_{SQ}$
  226 Oversampled sinogram
  228 First vector
  230 Second vector
  232 Third vector The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for acquiring tomographic image data comprising:
disposing an object in a detection range of a detection device having N detection elements arranged in at least one row where N is a positive integer;
detecting in a detection operation an intensity value for each of the detection elements by receiving transmitted waves or particles by each of the detection elements are repeated, where the waves or particles are detectable by the detection device, over (N+n) directions (n is an integer greater than or equal to 1) that are not overlapped with each other in relative detection directions for the waves or particles viewed from the object, while irradiation of the waves or particles toward the detection device by an emission device is performed, or while the waves or particles not generated by the emission device are transmitted through each part of the object;
obtaining a first vector with N×(N+n) elements from a detection signal by the detection device in the detection operation, wherein the elements of the first vector corresponding to those obtained by vectorizing an oversampled sinogram with (N+n) rows and N columns, each row and each column of which are associated with each detection direction and each detection element, respectively;
removing n×N elements corresponding a vector decimation order from the first vector to obtain a second vector having the remaining N×N elements;
operating a discrete inverse Radon transform matrix to the second vector to obtain a third vector having N×N elements; and
obtaining image data by de-vectorizing the third vector, for a two-dimensional tomographic image with N pixels×N pixels having a pixel arrangement that is stationary with respect to the object.

2. The method for acquiring tomographic image data according to claim 1, further comprising, before the removing the n×N elements from the first vector:
obtaining an oversampled system matrix having column—or row vectors of N×(N+n) elements, each of which elements has a weight value indicative of contribution of each pixel in the two-dimensional tomographic image to a path of a portion of the waves or particles, the portion going toward each of the N detection elements, which column—or row vectors are arranged in a column or a row direction according to each of the (N+n) detection directions while being associated with the pixels of the two-dimensional tomographic image; and obtaining a square system matrix by removing elements of n×N row vectors or column vectors corresponding to the vector decimation order in the oversampled system matrix.

3. The method for acquiring tomographic image data according to claim 2, further comprising, after the obtaining the square system matrix and before the operating the discrete inverse Radon transform matrix to the second vector:

obtaining the discrete inverse Radon transform matrix by calculating an inverse matrix of the square system matrix.

4. The method for acquiring tomographic image data according to claim 2, further comprising, after the obtaining the square system matrix and before the operating the discrete inverse Radon transform matrix to the second vector:

obtaining the discrete inverse Radon transform matrix by calculating a pseudo-inverse matrix of the square system matrix.

5. The method for acquiring tomographic image data according to claim 2, wherein the obtaining the square system matrix includes:

determining a sequence representing the vector decimation order from integer numbers of 1 to N×(N+n), wherein the sequence is an integer sequence having n×N elements obtained by removing N×N selected elements in the integer numbers from elements of integer numbers of 1 to N×(N+n).

6. The method for acquiring tomographic image data according to claim 5, wherein the obtaining the square system matrix further comprises:

determining a rank of the square system matrix obtained by removing elements at positions corresponding to the vector decimation order; and determining whether a value of the rank matches N×N or not.

7. The method for acquiring tomographic image data according to claim 2, wherein the obtaining the square system matrix includes:

determining a sequence representing the vector decimation order from integer numbers of 1 to N×(N+n), wherein the sequence is an integer sequence having n×N elements obtained by removing N×N elements in a continuous range terminating at s×N, where s is an integer greater than or equal to 1, from elements of integer numbers of 1 to N×(N+n).

8. The method for acquiring tomographic image data according to claim 7, wherein the detection operation is omitted in the detecting in the detection operation for detections corresponding to elements in the sequence representing the vector decimation order.

9. The method for acquiring tomographic image data according to claim 7, wherein the obtaining the square system matrix further comprises:

determining a rank of the square system matrix obtained by removing elements at positions corresponding to the vector decimation order; and determining whether a value of the rank matches N×N or not.

10. The method for acquiring tomographic image data according to claim 2, wherein the obtaining the square system matrix includes:

selecting a sequence representing the vector decimation order from integer numbers of 1 to N×(N+n), wherein the sequence is an integer sequence having n×N elements selected randomly without overlap.

11. The method for acquiring tomographic image data according to claim 10, wherein the obtaining the square system matrix further comprises:

determining a rank of the square system matrix obtained by removing elements at positions corresponding to the vector decimation order; and determining whether a value of the rank matches N×N or not.

12. The method for acquiring tomographic image data according to claim 2, wherein the obtaining the square system matrix includes:

selecting a sequence representing the vector decimation order from integer numbers of 1 to N×(N+n), wherein the sequence is an integer sequence having n×N elements of a continuous range starting at (s−1)×N+1, where s is an integer greater than or equal to 1.

13. The method for acquiring tomographic image data according to claim 12, wherein the obtaining the square system matrix further comprises:

determining a rank of the square system matrix obtained by removing elements at positions corresponding to the vector decimation order; and determining whether a value of the rank matches N×N or not.

14. The method for acquiring tomographic image data according to claim 12, wherein the detection operation is omitted in the detecting in the detection operation for detections corresponding to elements in the sequence representing the vector decimation order.

15. The method for acquiring tomographic image data according to claim 2, wherein the obtaining the square system matrix includes:

generating through a Gram-Schmidt orthogonalization process a group of N×N linear independent row—or column vectors from a set of row—or column vectors of elements in the oversampled system matrix and arranging the group of row—or column vectors in a column direction or a row direction for obtaining the square system matrix; and selecting for the vector decimation order a row number or a column number representing a row or a column not used for generating the group of the linear independent row—or column vectors in the row—or column vectors of the elements of the oversampled system matrix.

16. A tomographic image data acquisition device comprising:

a detection device having N detection elements arranged in at least one row where N is an integer greater than or equal to 1; and a control device that controls the detection device so that the detection device detects waves or particles after the waves or particles are transmitted each part of an object disposed in a detection range of the detection device by each of the detection elements in a detection direction, wherein the detection direction is changed with respect to the object while irradiation of the waves or particles toward the detection device by an emission device is performed, or while the waves or particles not generated by the emission device are transmitted through each part of the object and wherein the waves or particles are detectable by the detection device, wherein the tomographic image data acquisition device further comprises:

a decimation sequence storage unit that stores sequence data representing a decimation order; and a discrete inverse Radon transform matrix storage unit for storing a discrete inverse Radon transform matrix, and wherein the control device comprises:
- a discrete Radon transform processing unit for changing the detection direction over (N+n) directions that are not overlapped with each other in a relative detection direction for the waves or particles viewed from the object and for making the detection device output a detection signal for an oversampled sinogram with (N+n) rows and N columns, each row and each column of which are associated with each detection direction and each detection element, respectively;
- a vectorization processing unit for obtaining from the detection signal a first vector having N×(N+n) elements corresponding to those obtained by vectorizing the oversampled sinogram;
- a vector decimation processing unit for removing n×N elements according to a sequence data representing the decimation order from the first vector and for obtaining a second vector having the remaining N×N elements;
- a discrete inverse Radon transform processing unit for obtaining a third vector having N×N elements by operating the discrete inverse Radon transform matrix to the second vector; and
- an image data generation unit for de-vectorizing the third vector and for obtaining image data for a two-dimensional tomographic image with N pixels×N pixels having a pixel arrangement that is stationary with respect to the object.

17. The tomographic image data acquisition device according to claim 16, wherein the tomographic image data acquisition device further comprises:

an oversampled system matrix storage unit; and
a square system matrix storage unit, and
wherein the control device further comprises:
- an oversampled system matrix generation unit for obtaining an oversampled system matrix having column—or row vectors of N×(N+n) elements, each of which elements has a weight value indicative of contribution of each pixel in the two-dimensional tomographic image to a path of a portion of the waves or particles, the portion going toward each of the N detection elements, which column—or row vectors are arranged in a column or a row direction according to each of the (N+n) detection directions while being associated with the pixels of the two-dimensional tomographic image and for storing the oversampled system matrix into the oversampled system matrix storage unit;
- a matrix decimation processing unit for obtaining a square system matrix by removing elements of n×N row vectors or column vectors corresponding to the decimation order in the oversampled system matrix and for storing the square system matrix into the square system matrix storage unit; and
- an inverse matrix calculation unit for obtaining the discrete inverse Radon transform matrix by calculating an inverse matrix of the square system matrix and for storing the discrete inverse matrix into the discrete inverse Radon transform matrix storage unit.

18. The tomographic image data acquisition device according to claim 16 wherein the tomographic image data acquisition device further comprises:

an oversampled system matrix storage unit; and
a square system matrix storage unit, and
wherein the control device further comprises:
- an oversampled system matrix generation unit for obtaining an oversampled system matrix having column—or row vectors of N×(N+n) elements, each of which elements has a weight value indicative of contribution of each pixel in the two-dimensional tomographic image to a path of a portion of the waves or particles, the portion going toward each of the N detection elements, which column—or row vectors are arranged in a column or a row direction according to each of the (N+n) detection directions while being associated with the pixels of the two-dimensional tomographic image and for storing the oversampled system matrix into the oversampled system matrix storage unit;
- a matrix decimation processing unit for obtaining a square system matrix by removing elements of n×N row vectors or column vectors corresponding to the decimation order in the oversampled system matrix and for storing the square system matrix into the square system matrix storage unit; and
- a pseudo-inverse matrix calculation unit for obtaining the discrete inverse Radon transform matrix by calculating a pseudo-inverse matrix of the square system matrix and for storing the discrete inverse matrix into the discrete inverse Radon transform matrix storage unit.

19. A control program for an acquisition device of tomographic image data, the acquisition device having:

a detection device having N detection elements arranged in at least one row where N is a positive integer; and
a control device that controls the detection device so that the detection device detects waves or particles after the waves or particles are transmitted each part of an object disposed in a detection range of the detection device for the waves or particles by each of the detection elements in a detection direction, wherein relative detection direction for the waves or particles is changed with respect to the object while irradiation of the waves or particles toward the detection device by an emission device is performed, or while the waves or particles not generated by the emission device are transmitted through each part of the object and wherein the waves or particles are detectable by the detection device, wherein the control program makes the control device to perform:
- processing a discrete Radon transform in which the detection device is made to output a detection signal for an oversampled sinogram with (N+n) rows and N columns (n is an integer greater than or equal to 1), each row and each column of which are associated with each detection direction and each detection element, respectively, while changing the detection direction over (N+n) directions that are not overlapped with each other in a relative detection direction for the waves or particles viewed from the object;
- obtaining from the detection signal a first vector with N×(N+n) elements corresponding to those obtained by vectorizing oversampled sinogram;
- retrieving a sequence data representing a decimation order from a decimation sequence storage unit and obtaining a second vector having the remaining N×N elements by removing n×N elements from the first vector according to the sequence data;

retrieving a discrete inverse Radon transform matrix from a discrete inverse Radon transform matrix storage unit and obtaining a third vector having N×N elements by operating the discrete inverse Radon transform matrix to the second vector; and obtaining image data for a two-dimensional tomographic image of N pixels×N pixels having a pixel arrangement stationary with respect to the object by de-vectorizing the third vector.

20. The control program according to claim 19, further making the control device to perform:

obtaining an oversampled system matrix having column—or row vectors of N×(N+n) elements, each of which elements has a weight value indicative of contribution of each pixel in the two-dimensional tomographic image to a path of a portion of the waves or particles, the portion going toward each of the N detection elements, which column—or row vectors are arranged in a column or a row direction according to each of the (N+n) detection directions while being associated with the pixels of the two-dimensional tomographic image and storing the oversampled system matrix into an oversampled system matrix storage unit;

obtaining a square system matrix by removing elements of n×N row vectors or column vectors corresponding to the decimation order in the oversampled system matrix and storing the square system matrix into a square system matrix storage unit; and obtaining a discrete inverse Radon transform matrix by calculating an inverse matrix of the square system matrix and storing the discrete inverse Radon transform matrix into a discrete inverse Radon transform matrix storage unit.

* * * * *